(12) United States Patent
Gutsche et al.

(10) Patent No.: US 9,826,737 B2
(45) Date of Patent: Nov. 28, 2017

(54) SOLID FORMULATIONS OF CARBOXAMIDE ARTHROPODICIDES

(71) Applicant: E I DU PONT DE NEMOURS AND COMPANY, Wilmington, DE (US)

(72) Inventors: Oliver Walter Gutsche, Wilmington, DE (US); John Henry Green, Oxford, PA (US)

(73) Assignee: E I DU PONT DE NEMOURS AND COMPANY, Wilmington, DE (US)

( * ) Notice: Subject to any disclaimer, the term of this patent is extended or adjusted under 35 U.S.C. 154(b) by 0 days.

(21) Appl. No.: 14/018,786

(22) Filed: Sep. 5, 2013

(65) Prior Publication Data

US 2014/0005048 A1    Jan. 2, 2014

Related U.S. Application Data

(63) Continuation of application No. 12/596,676, filed as application No. PCT/US2008/067702 on Jun. 20, 2008, now abandoned.

(60) Provisional application No. 60/937,349, filed on Jun. 27, 2007.

(51) Int. Cl.
| | |
|---|---|
| *A01N 43/56* | (2006.01) |
| *A01N 25/08* | (2006.01) |
| *A01N 25/14* | (2006.01) |
| *A01N 25/30* | (2006.01) |
| *A01N 37/18* | (2006.01) |
| *A01N 25/00* | (2006.01) |
| *A01N 37/30* | (2006.01) |
| *A01N 41/02* | (2006.01) |
| *A01N 41/10* | (2006.01) |

(52) U.S. Cl.
CPC .............. *A01N 37/18* (2013.01); *A01N 25/00* (2013.01); *A01N 25/08* (2013.01); *A01N 25/14* (2013.01); *A01N 25/30* (2013.01); *A01N 37/30* (2013.01); *A01N 41/02* (2013.01); *A01N 41/10* (2013.01); *A01N 43/56* (2013.01)

(58) Field of Classification Search
CPC ........ A01N 37/18; A01N 41/10; A01N 37/30; A01N 25/14; A01N 25/08; A01N 43/56; A01N 41/02; A01N 25/30; A01N 25/00
See application file for complete search history.

(56) References Cited

U.S. PATENT DOCUMENTS

| | | | |
|---|---|---|---|
| 3,326,632 A * | 6/1967 | Hashizume | ............... B01J 20/12 |
| | | | 423/118.1 |
| 4,960,796 A | 10/1990 | Neubauer et al. | |
| 5,413,795 A | 5/1995 | Lee et al. | |
| 5,550,115 A | 8/1996 | Garst et al. | |
| 6,603,044 B1 | 8/2003 | Tohnishi et al. | |
| 6,747,047 B2 | 6/2004 | Lahm et al. | |
| 6,869,613 B2 | 3/2005 | Kimler | |
| 7,232,836 B2 | 6/2007 | Lahm et al. | |
| 7,247,647 B2 | 7/2007 | Hughes et al. | |
| 7,696,232 B2 | 4/2010 | Berger et al. | |
| 7,696,233 B2 | 4/2010 | Lahm et al. | |
| 8,709,513 B2 | 4/2014 | Gutsche et al. | |
| 2005/0215432 A1 * | 9/2005 | Schlatter | ................ A01N 47/40 |
| | | | 504/100 |
| 2006/0177474 A1 | 8/2006 | Kodama et al. | |
| 2007/0293550 A1 | 12/2007 | Rochling et al. | |
| 2008/0305093 A1 | 12/2008 | Gutsche et al. | |

FOREIGN PATENT DOCUMENTS

| | | |
|---|---|---|
| EP | 0107107 A1 | 5/1984 |
| EP | 1006107 A2 | 6/2000 |
| EP | 1717237 A1 | 11/2006 |
| JP | 07179302 A | 7/1995 |
| JP | 2001/2533801 A | 9/2001 |
| JP | 2005/336170 A | 12/2005 |
| WO | 93/14631 | 8/1993 |
| WO | 03/015519 A1 | 2/2003 |
| WO | 03/024222 A1 | 3/2003 |
| WO | WO 03024222 A1 * | 3/2003 |
| WO | 2004/067528 A1 | 8/2004 |
| WO | WO 2004067528 A1 * | 8/2004 |
| WO | 2005/104844 A1 | 11/2005 |

OTHER PUBLICATIONS

XP-002503851, AN 1995-280806, Database WPI Week 199537 Thomson Scientific, London, GB.
Infiltrate Definition. [online]. Merriam-Webster On-line Dictionary, 2009 [retrieved on May 16, 2013]. Retrieved from the Internet: <URL:HTTP://web.archive.org/web/20090423025633/http://www.merriam-webster.com/dictionary/infiltrate> 2 pages.

* cited by examiner

*Primary Examiner* — John Pak
*Assistant Examiner* — Andriae M Holt
(74) *Attorney, Agent, or Firm* — Linda D. Birch

(57) ABSTRACT

Disclosed is a solid arthropodicide composition comprising by weight
(a) from 0.3 to 100% of a particulate component comprising particles of a solid carrier infiltrated with a mixture comprising (i) one or more carboxamide arthropodicides and (ii) a surfactant constituent;
(b) from 0 to 50% of a surfactant component having dispersing and wetting properties; and
(c) from 0 to 99.7% of one or more additional formulating ingredients.

Also disclosed is a propagule contacted with a biologically effective amount of said composition.

13 Claims, No Drawings

SOLID FORMULATIONS OF CARBOXAMIDE ARTHROPODICIDES

FIELD OF THE INVENTION

This invention relates to certain solid formulations of carboxamide arthropodicides.

BACKGROUND OF THE INVENTION

The control of arthropod pests is extremely important in achieving high crop efficiency. Damage by arthropod pests to growing and stored agronomic crops can cause significant reduction in productivity and thereby result in increased costs to the consumer. The control of arthropod pests in forestry, greenhouse crops, ornamentals, nursery crops, stored food and fiber products, livestock, household, turf, wood products, and public and animal health is also important.

Anthranilamides (see U.S. Pat. No. 6,747,047, PCT Publications WO 2003/015519 and WO 2004/067528) and phthalic diamides (see U.S. Pat. No. 6,603,044) are recently discovered classes of carboxamide arthropodicides having activity against numerous arthropod pests of economic importance.

Typically chemical active ingredients for protecting plants, e.g., arthropodicides, are formulated as compositions (formulations) comprising the active compound(s) and inert ingredients such as carriers and adjuvants. These compositions can be applied by the user to the target pests or plants to be protected either in undiluted form or after dilution with water. Formulated compositions of plant protection products can be generally categorized as solid or liquid formulations. Liquid compositions include solutions (including emulsifiable concentrates), suspensions and emulsions (including microemulsions and/or suspoemulsions). Solid compositions include dusts, powders, granules, pellets, prills, pastilles and tablets. Each formulation type has advantages and disadvantages relative to other formulation types, and the optimal type for each application will depend upon the physical and biological characteristics of the active ingredient, and the conditions of storage and use, including pests to be controlled, plant parts or other locus to be protected, environmental conditions, etc.

The penetration and translaminar movement of arthropodicide active ingredients through the waxy leaf cuticle and epidermal cells, and their subsequent distribution in the mesophyll cells, vascular system and other tissues is particularly desirable for controlling arthropod pests that primarily obtain nourishment by extracting plant sap from the internal structures of plant parts such as leaves. Particularly noteworthy examples of such arthropod pests are piercing-sucking pests of the order Homoptera, such as members of the family Aleyrodidae (whiteflies), the family Aphidadae (aphids), the family Delphacidae (planthoppers) and the family Cicadellidae (leafhoppers). Also, penetration of arthropodicide active ingredients into propagules, including seeds, is desirable for controlling not only piercing-sucking pests but also chewing arthropod pests of the order Lepidoptera. Not only does penetration of the arthropodicide into the propagule protect the propagule, but if the arthropodicide is capable of translocation through plant vascular tissues, foliage developing from the propagule can be protected as well.

Active ingredients that are crystalline solids at room temperature can typically be easily formulated as solid compositions, because the brittle nature of crystalline solids facilitates milling operations to provide small crystals. In contrast, amorphous solids tend to smear and cake during milling. However, the attractive forces within the lattice of crystals thermodynamically impedes release of active ingredients for penetration into the waxy cuticle of a leaf or the testa of a seed.

Because carboxamide moieties are polar and support hydrogen-bonding, carboxamide arthropodicides are typically crystalline solids at room temperature. Accordingly they are generally easily formulated as solid compositions. Carboxamide arthropodicides also typically have low solubility in water. Therefore dilution in water of a solid formulation comprising a carboxamide arthropodicide typically forms a suspension of arthropodicide crystals that bind the active ingredient and thus retard absorption into plant tissues and limit efficacy in controlling sucking pests. Nevertheless, solid formulated compositions comprising a carboxamide arthropodicide active ingredient that release the active ingredient for penetration into a waxy leaf cuticle or seed testa have now been discovered.

SUMMARY OF THE INVENTION

This invention is directed to a solid arthropodicide composition comprising by weight
(a) from 0.3 to 100% of a particulate component comprising particles of a solid carrier infiltrated with a mixture comprising (i) one or more carboxamide arthropodicides and (ii) a surfactant constituent;
(b) from 0 to 50% of a surfactant component having dispersing and wetting properties; and
(c) from 0 to 99.7% of one or more additional formulating ingredients.

This invention also relates to a propagule contacted with a biologically effective amount of said composition.

DETAILED DESCRIPTION OF THE INVENTION

As used herein, the terms "comprises," "comprising," "includes," "including," "has," "having" or any other variation thereof, are intended to cover a non-exclusive inclusion. For example, a composition, process, method, article, or apparatus that comprises a list of elements is not necessarily limited to only those elements but may include other elements not expressly listed or inherent to such composition, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

As used herein, the term "silica" refers to a solid chemical substance consisting mostly (e.g., at least 90 or 95% by weight) of silicon and oxygen atoms in a ratio of about two oxygen atoms to one silicon atom, thus having the empirical formula of $SiO_2$. Silicas include, for example, precipitated silicas, fumed silicas, amorphous silicas, diatomaceous silicas (also known as diatomaceous earths) as well as silanized forms of these silicas. The term "silicate" refers to a solid chemical substance consisting mostly (e.g., at least 90 or 95% by weight) of atoms of silicon, oxygen and at least one metal (e.g., lithium, sodium, potassium, magnesium, calcium, aluminum).

As commonly known in the art, the term "saccharides" refers to chemical compounds that are either simple sugars (aldose or ketose monosaccharides) (e.g., glucose) or compounds in which simple sugars are connected together through glycosidic linkages to form disaccharides (e.g., sucrose, lactose), trisaccharides or polysaccharides. Polysaccharides include starches. Saccharides do not include compounds in which the substituents on the sugar molecule have been modified. For example, mannitol is not a sugar or saccharide, but can be regarded as a modified sugar or sugar derivative.

The term "pore" refers to a cavity in a particle (or particle agglomerate), the cavity having dimensions such that it is deeper than it is wide. Pores relevant to such measurements as pore diameter do not include closed pores (i.e. pores inaccessible to an external fluid and totally isolated from their neighbors). Accordingly, unless otherwise indicated in the present disclosure and claims, the term "pore" refers to an open pore (i.e. a pore accessible to a fluid external to the particulate component.) Pores allow infiltration (i.e. absorption) of a fluid into the interior of the particle. Intrusion volume is the volume of fluid that can be so accommodated per unit mass of the porous particulate. The unit used herein for intrusion volume is $cm^3/g$. Internal surface area is the aggregate surface area of the pores or cavities per unit mass of the porous particulate. The unit used herein for internal surface area is $m^2/g$. Mean pore diameter relates to the average diameter of the pores and is specified herein using the unit of μm (i.e. micron). As is well known in the art, intrusion volume, internal surface area and mean pore diameter of a porous substance can be measured using a mercury intrusion porosimeter, such as the model marketed by Porous Materials, Inc. (Ithaca, N.Y., USA). The values stated herein for intrusion volume, internal surface area and mean pore diameter refer to the values measured using a mercury intrusion porosimeter. For porosity measurements using a mercury intrusion porosimeter, cylindrical pores are assumed so that the mean pore diameter multiplied by the internal surface area equals the intrusion volume multiplied by 4.

As referred to in the present disclosure and claims, the term "propagule" means a seed or a regenerable plant part. The term "regenerable plant part" means a part of a plant other than a seed from which a whole plant may be grown or regenerated when the plant part is placed in horticultural or agricultural growing media such as moistened soil, peat moss, sand, vermiculite, perlite, rock wool, fiberglass, coconut husk fiber, tree fern fiber and the like, or even a completely liquid medium such as water. Regenerable plant parts commonly include rhizomes, tubers, bulbs and corms of such geophytic plant species as potato, sweet potato, yam, onion, dahlia, tulip, narcissus, etc. Regenerable plant parts include plant parts that are divided (e.g., cut) to preserve their ability to grow into a new plant. Therefore regenerable plant parts include viable divisions of rhizomes, tubers, bulbs and corms which retain meristematic tissue, such as an eye. Regenerable plant parts can also include other plant parts such as cut or separated stems and leaves from which some species of plants can be grown using horticultural or agricultural growing media. As referred to in the present disclosure and claims, unless otherwise indicated, the term "seed" includes both unsprouted seeds and sprouted seeds in which the testa (seed coat) still surrounds part of the emerging shoot and root.

Embodiments of the present invention include:

Embodiment 1

The composition described in the Summary of the Invention wherein constituent (i) (i.e. the one or more carboxamide arthropodicides in component (a), which is the particulate component comprising particles of a solid carrier infiltrated with a mixture comprising one or more carboxamide arthropodicides and a surfactant constituent) comprises a carboxamide arthropodicide comprising (at least) two vicinal carboxamide moieties bonded to carbon atoms.

Embodiment 1A

The composition described in the Summary of the Invention or Embodiment 1 wherein constituent (i) is selected from carboxamide arthropodicides that are ryanodine receptor ligands.

Embodiment 2

The composition described in the Summary of the Invention or Embodiment 1 or 1A wherein constituent (i) (i.e. the one or more carboxamide arthropodicides in component (a), which is the particulate component comprising particles of a solid carrier infiltrated with a mixture comprising one or more carboxamide arthropodicides and a surfactant constituent) is selected from anthranilamides of Formula 1, N-oxides, and salts thereof,

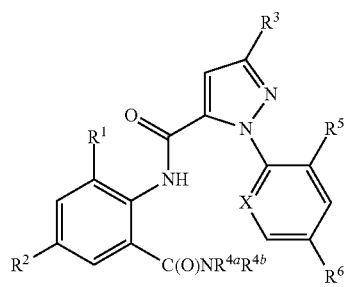

1 wherein
X is N, CF, CCl, CBr or CI;
$R^1$ is $CH_3$, Cl, Br or F;
$R^2$ is H, F, Cl, Br or —CN;
$R^3$ is F, Cl, Br, $C_1$-$C_4$ haloalkyl or $C_1$-$C_4$ haloalkoxy;
$R^{4a}$ is H, $C_1$-$C_4$ alkyl, cyclopropylmethyl or 1-cyclopropylethyl;
$R^{4b}$ is H or $CH_3$;
$R^5$ is H, F, Cl or Br; and
$R^6$ is H, F, Cl or Br.

Embodiment 2A

The composition of Embodiment 2 wherein constituent (i) is selected from anthranilamides of Formula 1, N-oxides, and salts thereof, wherein X is N; $R^1$ is $CH_3$; $R^2$ is Cl or —CN; $R^3$ is Cl, Br or $CF_3$; $R^{4a}$ is $C_1$-$C_4$ alkyl; $R^{4b}$ is H; $R^5$ is Cl; and $R^6$ is H.

Embodiment 2B

The composition of Embodiment 2A wherein constituent (i) is selected from anthranilamides of Formula 1, N-oxides, and salts thereof, wherein X is N; $R^1$ is $CH_3$; $R^2$ is Cl or —CN; $R^3$ is Cl, Br or $CF_3$; $R^{4a}$ is Me or $CH(CH_3)_2$; $R^{4b}$ is H; $R^5$ is Cl; and $R^6$ is H.

Embodiment 2C

The composition of Embodiment 2 wherein constituent (i) is selected from the group consisting of:
N-[4-chloro-2-methyl-6-[[(1-methylethyl)amino]carbonyl]phenyl]-1-(3-chloro-2-pyridinyl)-3-(trifluoromethyl)-1H-pyrazole-5-carboxamide,
N-[4-chloro-2-methyl-6-[(methylamino)carbonyl]phenyl]-1-(3-chloro-2-pyridinyl)-3-(trifluoromethyl)-1H-pyrazole-5-carboxamide,
3-bromo-N-[4-chloro-2-methyl-6-[[(1-methylethyl)amino]carbonyl]phenyl]-1-(3-chloro-2-pyridinyl)-1H-pyrazole-5-carboxamide,
3-bromo-N-[4-chloro-2-methyl-6-[(methylamino)carbonyl]phenyl]-1-(3-chloro-2-pyridinyl)-1H-pyrazole-5-carboxamide,
3-bromo-1-(3-chloro-2-pyridinyl)-N-[4-cyano-2-methyl-6-[(methylamino)-carbonyl]phenyl]-1H-pyrazole-5-carboxamide,
1-(3-chloro-2-pyridinyl)-N-[4-cyano-2-methyl-6-[(methylamino)carbonyl]-phenyl]-3-(trifluoromethyl)-1H-pyrazole-5-carboxamide,
3-bromo-1-(2-chlorophenyl)-N-[4-cyano-2-methyl-6-[[(1-methylethyl)-amino]carbonyl]phenyl]-1H-pyrazole-5-carboxamide,
3-bromo-1-(2-chlorophenyl)-N-[4-cyano-2-methyl-6-[(methylamino)-carbonyl]phenyl]-1H-pyrazole-5-carboxamide,
3-bromo-1-(2-chlorophenyl)-N-[2,4-dichloro-6-[(methylamino)carbonyl]-phenyl]-1H-pyrazole-5-carboxamide,
3-bromo-N-[4-chloro-2-[[(cyclopropylmethyl)amino]carbonyl]-6-methyl-phenyl]-1-(3-chloro-2-pyridinyl)-1H-pyrazole-5-carboxamide,
3-bromo-1-(3-chloro-2-pyridinyl)-N-[4-cyano-2-[[(cyclopropylmethyl)-amino]-carbonyl]-6-methylphenyl]-1H-pyrazole-5-carboxamide,
3-bromo-N-[4-chloro-2-[[(1-cyclopropylethyl)amino]carbonyl]-6-methyl-phenyl]-1-(3-chloro-2-pyridinyl)-1H-pyrazole-5-carboxamide, and
3-bromo-1-(3-chloro-2-pyridinyl)-N-[4-cyano-2-[[(1-cyclopropylethyl)-amino]carbonyl]-6-methylphenyl]-1H-pyrazole-5-carboxamide.

Embodiment 2D

The composition of any one of Embodiments 2 through 2C wherein component (a) comprises 3-bromo-1-(3-chloro-2-pyridinyl)-N-[4-cyano-2-methyl-6-[(methylamino)carbonyl]phenyl]-1H-pyrazole-5-carboxamide.

Embodiment 2E

The composition of any one of Embodiments 2 through 2C wherein component (a) comprises 3-bromo-N-[4-chloro-2-methyl-6-[(methylamino)carbonyl]phenyl]-1-(3-chloro-2-pyridinyl)-1H-pyrazole-5-carboxamide.

Embodiment 3

The composition described in the Summary of the Invention or Embodiment 1 or 1A wherein constituent (i) is selected from phthalic diamides of Formula 2 and salts thereof, wherein
$R^{11}$ is $CH_3$, Cl, Br or I;
$R^{12}$ is $CH_3$ or Cl;
$R^{13}$ is $C_1$-$C_3$ fluoroalkyl;
$R^{14}$ is H or $CH_3$;
$R^{15}$ is H or $CH_3$;
$R^{16}$ is $C_1$-$C_2$ alkyl; and
n is 0, 1 or 2.

Embodiment 3A

The composition of Embodiment 3 wherein constituent (i) is selected from phthalic diamides of Formula 2 and salts thereof, wherein $R^{11}$ is Cl, Br or I; $R^{12}$ is $CH_3$; $R^{13}$ is $CF_3$, $CF_2CF_3$ or $CF(CF_3)_2$; and $R^{16}$ is $CH_3$.

Embodiment 3B

The composition of described in the Summary of the Invention or Embodiment 1 or 1A wherein constituent (i) is $N^2$-[1,1-dimethyl-2-(methylsulfonyl)ethyl]-3-iodo-$N^1$-[2-methyl-4-[1,2,2,2-tetrafluoro-1-(trifluoromethyl)ethyl]phenyl]-1,2-benzenedicarboxamide.

Embodiment 3C

The composition of described in the Summary of the Invention or Embodiment 1 or 1A wherein component (a) comprises $N^2$-[1,1-dimethyl-2-(methylsulfonyl)ethyl]-3-iodo-$N^1$-[2-methyl-4-[1,2,2,2-tetrafluoro-1-(trifluoromethyl)ethyl]phenyl]-1,2-benzenedicarboxamide.

Embodiment 4

The composition described in the Summary of the Invention or any one of Embodiments 1 through 3B wherein constituent (i) (i.e. the one or more carboxamide arthropodicides in component (a), which is the particulate component comprising particles of a solid carrier infiltrated with a mixture comprising one or more carboxamide arthropodicides and a surfactant constituent) has a melting point above about 80° C. (neat, in the absence of other constituents or components).

Embodiment 4A

The composition of Embodiment 4 wherein constituent (i) has a melting point above about 100° C.

Embodiment 4B

The composition of Embodiment 4A wherein constituent (i) has a melting point above about 120° C.

Embodiment 4C

The composition of Embodiment 4B wherein constituent (i) has a melting point above about 160° C.

Embodiment 4D

The composition of Embodiment 4C wherein constituent (i) has a melting point above about 180° C.

Embodiment 4E

The composition of Embodiment 4D wherein constituent (i) has a melting point above about 200° C.

Embodiment 5

The composition described in the Summary of the Invention or any one of Embodiments 1 through 4E wherein the mean particle size (i.e. volume moment mean, De Brouker mean) of the particles of the solid carrier in component (a) (i.e. the particulate component comprising particles of a solid carrier infiltrated with a water-immiscible liquid constituent) is at least about 0.1 μm.

Embodiment 5A

The composition of Embodiment 5 wherein the mean particle size of the particles of the solid carrier in component (a) is at least about 5 μm.

Embodiment 6

The composition described in the Summary of the Invention or any one of Embodiments 1 through 5A wherein the mean particle size of the particles of the solid carrier in component (a) is no more than about 200 μm.

Embodiment 6A

The composition of Embodiment 6 wherein the mean particle size of particles of the solid carrier in component (a) is no more than about 20 μm.

Embodiment 7

The composition described in the Summary of the Invention or any one of Embodiments 1 through 6A wherein the solid carrier in component (a) has a mean pore diameter of at least about 0.05 μm.

Embodiment 7A

The composition of Embodiment 7 wherein the solid carrier in component (a) has a mean pore diameter of at least about 0.1 μm.

Embodiment 8

The composition described in the Summary of the Invention or any one of Embodiments 1 through 7A wherein the solid carrier in component (a) has a mean pore diameter of no more than about 2 μm.

Embodiment 8A

The composition of Embodiment 8 wherein the solid carrier in component (a) has a mean pore diameter of no more than about 1 μm.

Embodiment 8B

The composition of Embodiment 8A wherein the solid carrier in component (a) has a mean pore diameter of no more than about 0.5 μm.

Embodiment 9

The composition described in the Summary of the Invention or any one of Embodiments 1 through 8B wherein the solid carrier in component (a) has an internal surface area of at least about 1 m$^2$/g.

Embodiment 9A

The composition of Embodiment 9 wherein the solid carrier in component (a) has an internal surface area of at least about 20 m$^2$/g.

Embodiment 9B

The composition of Embodiment 9A wherein the solid carrier in component (a) has an internal surface area of at least about 80 m$^2$/g.

Embodiment 9C

The composition of Embodiment 9B wherein the solid carrier in component (a) has an internal surface area of at least about 90 m$^2$/g.

Embodiment 9D

The composition of Embodiment 9C wherein the solid carrier in component (a) has an internal surface area of at least about 100 m$^2$/g.

Embodiment 10

The composition described in the Summary of the Invention or any one of Embodiments 1 through 9D wherein the solid carrier in component (a) has an internal surface area of no more than about 600 m$^2$/g.

Embodiment 10A

The composition of Embodiment 10 wherein the solid carrier in component (a) has an internal surface area of no more than about 400 m$^2$/g.

Embodiment 10B

The composition of Embodiment 10A wherein the solid carrier in component (a) has an internal surface area of no more than about 200 m$^2$/g.

Embodiment 11

The composition described in the Summary of the Invention or any one of Embodiments 1 through 10B wherein the solid carrier in component (a) has an intrusion volume of at least about 1 cm$^3$/g.

Embodiment 11A

The composition of Embodiment 11 wherein the solid carrier in component (a) has an intrusion volume of at least about 2 cm$^3$/g.

Embodiment 11B

The composition of Embodiment 11A wherein the solid carrier in component (a) has an intrusion volume of at least about 3 cm$^3$/g.

Embodiment 11C

The composition of Embodiment 11B wherein the solid carrier in component (a) has an intrusion volume of at least about 4 cm$^3$/g.

Embodiment 11D

The composition of Embodiment 11C wherein the solid carrier in component (a) has an intrusion volume of at least about 5 cm$^3$/g.

Embodiment 12

The composition described in the Summary of the Invention or any one of Embodiments 1 through 11D wherein the solid carrier in component (a) has an intrusion volume of no more than about 20 cm$^3$/g.

Embodiment 12A

The composition of Embodiment 12 wherein the solid carrier in component (a) has an intrusion volume of no more than about 10 cm$^3$/g.

Embodiment 13

The composition described in the Summary of the Invention or any one of Embodiments 1 through 12A wherein the solid carrier in component (a) comprises at least one silica or silicate.

Embodiment 13A

The composition of Embodiment 13 wherein the solid carrier in component (a) comprises at least one silica or silicate selected from the group consisting of silicas and silicates of lithium, sodium, potassium, magnesium, calcium and aluminum (including mixtures thereof).

Embodiment 13B

The composition of Embodiment 13A wherein the solid carrier in component (a) comprises at least one silica or silicate selected from the group consisting of silicas and silicates of magnesium, calcium and aluminum (including mixtures thereof).

Embodiment 13C

The composition of Embodiment 13B wherein the solid carrier in component (a) comprises calcium silicate.

Embodiment 14

The composition described in the Summary of the Invention or any one of Embodiments 1 through 13C wherein the solid carrier has water solubility at 20° C. of not more than about 10 g/L.

Embodiment 14A

The composition of Embodiment 14 wherein the solid carrier has water solubility at 20° C. of not more than about 5 g/L.

Embodiment 14B

The composition of Embodiment 14A wherein the solid carrier has water solubility at 20° C. of not more than about 2 g/L.

Embodiment 14C

The composition of Embodiment 14B wherein the solid carrier has water solubility at 20° C. of not more than about 1 g/L.

Embodiment 15

The composition described in the Summary of the Invention or any one of Embodiments 1 through 14C wherein the surfactant constituent in component (a) comprises one or more surfactants that inhibit the crystallization of at least one carboxamide arthropodicide in component (a).

Embodiment 15A

The composition described in the Summary of the Invention or any one of Embodiments 1 through 15 wherein constituent (i) (i.e. the one or more carboxamide arthropodicides) in the mixture infiltrated into the solid carrier is at least about 50% amorphous.

Embodiment 15B

The composition of Embodiment 15A wherein constituent (i) is at least about 80% amorphous.

Embodiment 15C

The composition of Embodiment 15B wherein constituent (i) is at least about 90% amorphous.

Embodiment 15D

The composition of Embodiment 15C wherein constituent (i) is at least about 95% amorphous.

Embodiment 15E

The composition described in the Summary of the Invention or any one of Embodiments 1 through 15D wherein the mixture comprising constituent (i) (i.e. the one or more carboxamide arthropodicides) and constituent (ii) (i.e. the surfactant constituent) is amorphous (i.e. not crystalline).

Embodiment 15F

The composition described in the Summary of the Invention or any one of Embodiments 1 through 15E wherein the surfactant constituent comprises one or more surfactants selected from the group consisting of alkylbenzenesulfonic acids and their salts, alkylpolyglycosides, hydroxylalkylcelluloses, ethylene oxide-propylene oxide block copolymers, vinylpyrrolidone polymers, ethoxylated sorbitan esters and ethoxylated sorbitol esters.

Embodiment 15G

The composition of Embodiment 15F wherein the surfactant constituent comprises one or more surfactants selected from the group consisting of alkylbenzenesulfonic acids and their salts, alkylpolyglycosides, ethylene oxide-propylene oxide block copolymers, and ethoxylated sorbitol esters.

Embodiment 16

The composition described in the Summary of the Invention or any one of Embodiments 1 through 15G wherein the weight ratio of the mixture comprising the one or more carboxamide arthropodicides and the surfactant constituent in component (a) to the solid carrier in component (a) is at least about 1:2.

Embodiment 16A

The composition of Embodiment 16 wherein the weight ratio of the mixture to the solid carrier in component (a) is at least about 2:3.

Embodiment 17

The composition described in the Summary of the Invention or any one of Embodiments 1 through 16A wherein the weight ratio of the mixture comprising the one or more carboxamide arthropodicides and the surfactant constituent in component (a) to the solid carrier in component (a) is no more than about 5:1.

Embodiment 17A

The composition of Embodiment 17 wherein the weight ratio of the mixture to the solid carrier in component (a) is no more than about 4:1.

Embodiment 17B

The composition of Embodiment 17A wherein the weight ratio of the mixture to the solid carrier in component (a) is no more than about 3:1.

Embodiment 17C

The composition of Embodiment 17B wherein the weight ratio of the mixture to the solid carrier in component (a) is no more than about 2:1.

Embodiment 18

The composition described in the Summary of the Invention or any one of Embodiments 1 through 17C wherein the weight ratio of constituent (ii) (i.e. the surfactant constituent) to constituent (i) (i.e. the one or more carboxamide arthropodicides) in component (a) is at least about 1:2.

Embodiment 18A

The composition of Embodiment 18 wherein the weight ratio of constituent (ii) to constituent (i) is at least about 1:1.

Embodiment 19

The composition described in the Summary of the Invention or any one of Embodiments 1 through 18A wherein the weight ratio of constituent (ii) to constituent (i) is no more than about 50:1.

Embodiment 19A

The composition of Embodiment 19 wherein the weight ratio of constituent (ii) to constituent (i) is no more than about 5:1.

Embodiment 19B

The composition of Embodiment 19A wherein the weight ratio of constituent (ii) to constituent (i) is no more than about 2:1.

Embodiment 20

The composition described in the Summary of the Invention or any one of Embodiments 1 through 19B wherein component (a) is at least about 1% of the composition by weight.

Embodiment 20A

The composition of Embodiment 20 wherein component (a) is at least about 10% of the composition by weight.

Embodiment 21

The composition described in the Summary of the Invention or any one of Embodiments 1 through 20A wherein component (a) is no more than about 80% of the composition by weight.

Embodiment 21A

The composition of Embodiment 21 wherein component (a) is no more than about 60% of the composition by weight.

Embodiment 22

The composition described in the Summary of the Invention or any one of Embodiments 1 through 21A wherein component (b) (i.e. the surfactant component having dispersing and wetting properties) comprises one or more surfactants selected from the group consisting of alkylnaphthalenesulfonates (i.e. salts of alkylnaphthalenesulfonic acids), salts of naphthalene formaldehyde condensate sulfonates (i.e. salts of sulfonated naphthalene formaldehyde condensates), and lignosulfonates (i.e. salts of lignosulfonic acid).

Embodiment 22A

The composition of Embodiment 22 wherein component (b) comprises one or more lignosulfonates.

Embodiment 22B

The composition of Embodiment 22A wherein component (b) comprises one or more sodium, potassium or calcium lignosulfonates.

Embodiment 23

The composition described in the Summary of the Invention or any one of Embodiments 1 through 22B wherein component (b) is at least about 1% of the composition by weight.

Embodiment 23A

The composition of Embodiment 23 wherein component (b) is at least about 3% of the composition by weight.

Embodiment 24

The composition described in the Summary of the Invention or any one of Embodiments 1 through 23A wherein component (b) is no more than about 30% of the composition by weight.

Embodiment 24A

The composition of Embodiment 24 wherein component (b) is no more than about 15% of the composition by weight.

Embodiment 25

The composition described in the Summary of the Invention or any one of Embodiments 1 through 24A wherein component (c) (i.e. the one or more additional formulating ingredients) comprises one or more formulating ingredients selected from the group consisting of lubricants, anticaking agents, chemical stabilizers, adhesive agents, film-forming agents and solid diluents.

Embodiment 25A

The composition described in the Summary of the Invention or any one of Embodiments 1 through 25 wherein component (c) comprises one or more formulating ingredients selected from the group consisting of lubricants, anticaking agents, chemical stabilizers and solid diluents

Embodiment 25B

The composition described in the Summary of the Invention or any one of Embodiments 1 through 25A wherein component (c) comprises one or more formulating ingredients selected from the group consisting of grinding agents, binders, film-forming agents, adhesive agents and water-soluble diluents.

Embodiment 25C

The composition of Embodiment 25B wherein component (c) comprises one or more formulating ingredients selected from the group consisting of grinding agents, binders and water-soluble diluents.

Embodiment 25D

The composition described in the Summary of the Invention or any one of Embodiments 1 through 25C wherein component (c) comprises one or more clays in an amount ranging from about 1 to about 15% of the composition by weight.

Embodiment 25E

The composition described in the Summary of the Invention or any one of Embodiments 1 through 25C wherein component (c) comprises one or more saccharides in an amount ranging from about 1 to about 85% of the composition by weight.

Embodiment 25F

The composition of Embodiment 25E wherein component (c) comprises one or more saccharides in an amount ranging from about 5 to about 35% of the composition by weight.

Embodiment 25G

The composition of Embodiment 25F wherein component (c) comprises one or more saccharides in an amount ranging from about 5 to about 25% of the composition by weight.

Embodiment 25H

The composition of Embodiment 25E wherein component (c) comprises lactose monohydrate in an amount ranging from about 1 to about 80% of the composition by weight.

Embodiment 25I

The composition of Embodiment 25H wherein component (c) comprises lactose monohydrate in an amount ranging from about 1 to about 35% of the composition by weight.

Embodiment 25J

The composition of Embodiment 25I wherein component (c) comprises lactose monohydrate in an amount ranging from about 1 to about 25% of the composition by weight.

Embodiment 25K

The composition of Embodiment 25E wherein component (c) comprises sucrose in an amount ranging from about 0.1 to about 5% of the composition by weight.

Embodiment 26

The composition described in the Summary of the Invention or any one of Embodiments 1 through 25J 25K wherein component (c) is at least about 1% of the composition by weight.

Embodiment 26B

The composition of Embodiment 26 wherein component (c) is at least about 20% of the composition by weight.

Embodiment 27

The composition described in the Summary of the Invention or any one of Embodiments 1 through 26B wherein component (c) is no more than about 80% of composition by weight.

Embodiment 27A

The composition of Embodiment 27 wherein component (c) is no more than about 70% of the composition by weight.

Embodiment 28

The composition described in the Summary of the Invention or any one of Embodiments 1 through 27A wherein component (c) comprises an adhesive or film former constituent in an amount of at least about 1% of the composition by weight.

Embodiment 28A

The composition of Embodiment 28 wherein the adhesive or film former constituent is at least about 3% of the composition by weight.

Embodiment 28B

The composition of Embodiment 28A wherein the adhesive or film former constituent is least about 9% of the composition by weight.

Embodiment 28C

The composition of any one of Embodiments 28 through 28B wherein the adhesive or film former constituent is no more than about 90% of the composition by weight.

Embodiment 28D

The composition of Embodiment 28C wherein the adhesive or film former constituent is no more than about 75% of the composition by weight.

Embodiment 28E

The composition of Embodiment 28D wherein the adhesive or film former constituent is no more than about 50% of the composition by weight.

Embodiment 29

A propagule contacted with a biologically effective amount of the composition described in the Summary of the Invention or any one of Embodiments 28 through 28E.

Embodiment 29A

The propagule of Embodiment 29 which is a seed.

Embodiment 29B

The propagule of Embodiment 29A which is a seed of wheat, durum wheat, barley, oat, rye, maize, sorghum, rice, wild rice, cotton, flax, sunflower, soybean, garden bean, lima bean, broad bean, garden pea, peanut, alfalfa, beet, garden lettuce, rapeseed, cole crop, turnip, leaf mustard, black mustard, tomato, potato, pepper, eggplant, tobacco, cucumber, muskmelon, watermelon, squash, carrot, zinnia, cosmos, chrysanthemum, sweet scabious, snapdragon, gerbera, babys-breath, statice, blazing star, lisianthus, yarrow, marigold, pansy, impatiens, petunia, geranium or coleus.

Embodiment 29C

The propagule of Embodiment 29B which is a seed of cotton, maize, soybean or rice.

Embodiment 29D

The propagule of Embodiment 29 which is a rhizome, tuber, bulb or corm, or viable division thereof.

Embodiment 29E

The propagule of Embodiment 29D which is a rhizome, tuber, bulb or corm, or viable division thereof, of potato, sweet potato, yam, garden onion, tulip, gladiolus, lily, narcissus, dahlia, iris, crocus, anemone, hyacinth, grape-hyacinth, freesia, ornamental onion, wood-sorrel, squill, cyclamen, glory-of-the-snow, striped squill, calla lily, gloxinia or tuberous begonia.

Embodiment 29F

The propagule of Embodiment 29E which is a rhizome, tuber, bulb or corm, or viable division thereof, of potato, sweet potato, garden onion, tulip, daffodil, crocus or hyacinth.

Embodiment 29G

The propagule of Embodiment 29 which is a stem or leaf cutting.

Embodiments of this invention can be combined in any manner.

The term "carboxamide arthropodicide" in the present context denotes a compound useful for controlling arthropod pests which comprises one or more carboxamide moieties in its molecular structure. Because carboxamide moieties are polar and support hydrogen-bonding, carboxamide arthropodicides are typically crystalline solids in their pure form at room temperature (e.g., 20° C.). Although the present invention is not limited to carboxamide arthropodicides that are crystalline solids at room temperature, it is particularly well suited and advantageous for them. Therefore typically at least one of the one or more carboxamide arthropodicides of constituent (i) has a melting point higher than about 20° C., more typically higher than about 50° C., more typically higher than about 80° C., even more typically above about 100° C., and most typically above about 120, 160, 180 or even 200° C. Usually all of the one or more carboxamide arthropodicides of constituent (i) have melting points higher than about 80° C., above about 100° C., or even above about 120, 160, 180 or 200° C. Typically the one or more carboxamide arthropodicides of constituent (i) have water solubility less than about 10 g/L and more typically less than about 5 g/L.

As is well known in the art, the term "carboxamide" refers to a moiety comprising a carbon, nitrogen and oxygen atom bonded in the configuration shown as Formula A. The carbon atom in Formula A is bonded to a carbon atom in a radical to which the carboxamide moiety is bonded. The nitrogen atom in Formula A is bonded to the carbonyl carbon of Formula A and also bonded to two other atoms, at least one atom of which is selected from a hydrogen atom or a carbon atom of another radical to which the carboxamide moiety is bonded.

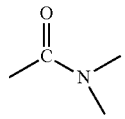

A

In one embodiment the present compositions comprise at least one carboxamide arthropodicide that is solid at room temperature and contains at least two carboxamide moieties. In another embodiment at least one carboxamide arthropodicide contains at least two carboxamide moieties vicinally bonded to carbon atoms (i.e. in ortho arrangement, and in other words, two vicinal carboxamide moieties bonded to carbon atoms) of a carbocyclic or heterocyclic ring. Thereby each carboxamide moiety can be independently bonded through the carbonyl carbon of Formula A or the nitrogen atom of Formula A to a carbon atom of the carbocyclic or heterocyclic ring. Accordingly each carboxamide moiety in the vicinal arrangement can be bonded through the carbonyl carbon, or each carboxamide moiety can be bonded through the nitrogen atom, or one carboxamide moiety can be bonded through the carbonyl carbon and the other carboxamide moiety can be bonded through the nitrogen atom. The presence of two vicinal carboxamide moieties in the molecular structure can provide strong crystal lattice attractions and relatively high melting points. In a further embodiment the carbocyclic or heterocyclic ring of at least one carboxamide arthropodicide is aromatic (i.e. satisfies the Hückel 4n+2 rule for aromaticity).

Of particular note as carboxamide arthropodicides useful in compositions of the present invention are those of Formula 1, N-oxides and salts thereof, and Formula 2 and salts thereof

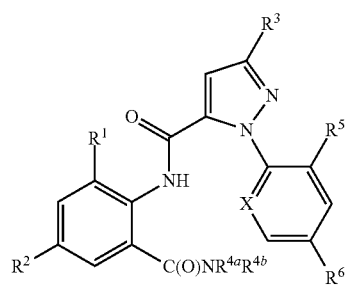

1 wherein
X is N, CF, CCl, CBr or Cl;
$R^1$ is $CH_3$, Cl, Br or F;
$R^2$ is H, F, Cl, Br or —CN;
$R^3$ is F, Cl, Br, $C_1$-$C_4$ haloalkyl or $C_1$-$C_4$ haloalkoxy;
$R^{4a}$ is H, $C_1$-$C_4$ alkyl, cyclopropylmethyl or 1-cyclopropylethyl;
$R^{4b}$ is H or $CH_3$;
$R^5$ is H, F, Cl or Br; and
$R^6$ is H, F, Cl or Br.

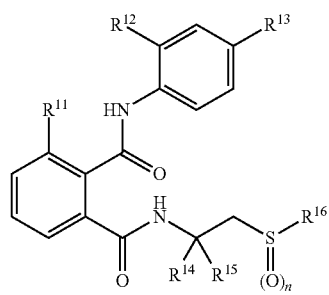

2 wherein
$R^{11}$ is $CH_3$, Cl, Br or I;
$R^{12}$ is $CH_3$ or Cl;
$R^{13}$ is $C_1$-$C_3$ fluoroalkyl;
$R^{14}$ is H or $CH_3$;
$R^{15}$ is H or $CH_3$;
$R^{16}$ is $C_1$-$C_2$ alkyl; and
n is 0, 1 or 2.

In the above recitations, the term "alkyl", used either alone or in compound words such as "haloalkyl" or "fluoroalkyl" includes straight-chain or branched alkyl, such as, methyl, ethyl, n-propyl, i-propyl, or the different butyl isomers. "Alkoxy" includes, for example, methoxy, ethoxy, n-propyloxy, isopropyloxy and the different butoxy isomers. The term "halogen", either alone or in compound words such as "haloalkyl", includes fluorine, chlorine, bromine or iodine. Further, when used in compound words such as "haloalkyl" or "haloalkoxy", said alkyl may be partially or fully substituted with halogen atoms which may be the same or different. Examples of "haloalkyl" include $CF_3$, $CH_2Cl$, $CH_2CF_3$ and $CCl_2CF_3$. The terms "haloalkoxy", and the like, are defined analogously to the term "haloalkyl". Examples of "haloalkoxy" include $OCF_3$, $OCH_2Cl_3$, $OCH_2CH_2CHF_2$ and $OCH_2CF_3$.

The total number of carbon atoms in a substituent group is indicated by the "$C_i$-$C_j$" prefix where i and j are numbers from 1 to 4. For example, $C_1$-$C_4$ alkyl designates methyl through butyl, including the various isomers.

Compounds of Formula 1 and Formula 2 wherein substituents are as specified above each have vicinal carboxamide substituents bonded to the carbon atoms of a phenyl ring. In Formula 1 one carboxamide moiety is bonded through the carbonyl carbon and the other carboxamide moiety is bonded through the nitrogen atom, and in Formula 2 both carboxamide moieties are bonded through the carbonyl carbon to the phenyl ring supporting the vicinal positioning of the carboxamide moieties. The arthropodicidal activity of the Formula 1 and Formula 2 compounds is believed to involve binding to ryanodine receptors in muscle cells, causing the channel to open and release calcium ions into the cytoplasm. Depletion of calcium ion stores results in arthropod paralysis and death. Accordingly, carboxamide arthropodicide compounds of Formulae 1 and 2 are described as ryanodine receptor ligands. PCT Publication WO 2004/027042 describes an assay for ryanodine receptor ligands. Partly because of the two carboxamide moieties in their molecular structures, compounds of Formulae 1 and 2 in their pure states are typically crystalline solids with relatively high melting points, i.e. above about 150° C., and often above even 200° C. Accordingly, the composition of the present invention can facilitate the arthropodicidal efficacy of these compounds. Therefore of note is the composition of the present invention wherein constituent (i) (i.e.

the one or more carboxamide arthropodicides in component (a)) comprises at least one carboxamide arthropodicide that is a ryanodine receptor ligand. Also of note is the composition of the present invention wherein constituent (i) is selected from carboxamide arthropodicides that are ryanodine receptor ligands. Compounds of Formulae 1 and 2 and methods for their preparation are reported in the patent literature; see, for example, U.S. Pat. No. 6,747,047, and PCT Publications WO 2003/015518, WO 2003/015519 and WO 2004/067528 regarding Formula 1, and U.S. Pat. No. 6,603,044 regarding Formula 2.

Of particular note is the composition described in the Summary of the Invention wherein constituent (i) (i.e. the one or more carboxamide arthropodicides) comprises a carboxamide arthropodicide selected from the group consisting of:

3-bromo-1-(3-chloro-2-pyridinyl)-N-[4-cyano-2-methyl-6-[(methylamino)carbonyl]-phenyl]-1H-pyrazole-5-carboxamide (Formula 1), 3-bromo-N-[4-chloro-2-methyl-6-[(methylamino)carbonyl]phenyl]-1-(3-chloro-2-pyridinyl)-1H-pyrazole-5-carboxamide (Formula 1), N-[4-chloro-2-methyl-6-[[(1-methylethyl)amino]carbonyl]phenyl]-1-(3-chloro-2-pyridinyl)-3-(trifluoromethyl)-1H-pyrazole-5-carboxamide (Formula 1), N-[4-chloro-2-methyl-6-[(methylamino)carbonyl]phenyl]-1-(3-chloro-2-pyridinyl)-3-(trifluoromethyl)-1H-pyrazole-5-carboxamide (Formula 1), 3-bromo-N-[4-chloro-2-methyl-6-[[(1-methylethyl)amino]carbonyl]phenyl]-1-(3-chloro-2-pyridinyl)-1H-pyrazole-5-carboxamide (Formula 1), 1-(3-chloro-2-pyridinyl)-N-[4-cyano-2-methyl-6-[(methylamino)carbonyl]phenyl]-3-(trifluoromethyl)-1H-pyrazole-5-carboxamide (Formula 1), 3-bromo-1-(2-chlorophenyl)-N-[4-cyano-2-methyl-6-[[(1-methylethyl)amino]-carbonyl]-phenyl]-1H-pyrazole-5-carboxamide (Formula 1), 3-bromo-1-(2-chlorophenyl)-N-[4-cyano-2-methyl-6-[(methylamino)carbonyl]phenyl]-1H-pyrazole-5-carboxamide (Formula 1), 3-bromo-1-(2-chlorophenyl)-N-[2,4-dichloro-6-[(methylamino)carbonyl]phenyl]-1H-pyrazole-5-carboxamide (Formula 1), 3-bromo-N-[4-chloro-2-[[(cyclopropylmethyl)amino]carbonyl]-6-methylphenyl]-1-(3-chloro-2-pyridinyl)-1H-pyrazole-5-carboxamide (Formula 1), 3-bromo-1-(3-chloro-2-pyridinyl)-N-[4-cyano-2-[[(cyclopropylmethyl)amino]-carbonyl]-6-methylphenyl]-1H-pyrazole-5-carboxamide (Formula 1), 3-bromo-N-[4-chloro-2-[[(1-cyclopropylethyl)amino]carbonyl]-6-methylphenyl]-1-(3-chloro-2-pyridinyl)-1H-pyrazole-5-carboxamide (Formula 1), 3-bromo-1-(3-chloro-2-pyridinyl)-N-[4-cyano-2-[[(1-cyclopropylethyl)amino]carbonyl]-6-methylphenyl]-1H-pyrazole-5-carboxamide (Formula 1), and $N^2$-[1,1-dimethyl-2-(methylsulfonyl)ethyl]-3-iodo-$N^1$-[2-methyl-4-[1,2,2,2-tetrafluoro-1-(trifluoromethyl)ethyl]phenyl]-1,2-benzenedicarboxamide.

Of particular note as carboxamide arthropodicides in the present composition are 3-bromo-1-(3-chloro-2-pyridinyl)-N-[4-cyano-2-methyl-6-[(methylamino)carbonyl]phenyl]-1H-pyrazole-5-carboxamide and 3-bromo-N-[4-chloro-2-methyl-6-[(methylamino)carbonyl]-phenyl]-1-(3-chloro-2-pyridinyl)-1H-pyrazole-5-carboxamide.

The carboxamide arthropodicides (e.g., Formula 1) in the present compositions can also be in the form of N-oxides. One skilled in the art will appreciate that not all nitrogen-containing heterocyclic rings can form N-oxides since the nitrogen requires an available lone pair for oxidation to the oxide; one skilled in the art will recognize those nitrogen-containing heterocyclic rings which can form N-oxides. One skilled in the art will also recognize that tertiary amines can form N-oxides. Synthetic methods for the preparation of N-oxides of heterocyclic rings and tertiary amines are very well known by one skilled in the art including the oxidation of heterocyclic rings and tertiary amines with peroxy acids such as peracetic and m-chloroperbenzoic acid (MCPBA), hydrogen peroxide, alkyl hydroperoxides such as t-butyl hydroperoxide, sodium perborate, and dioxiranes such as dimethyldioxirane. These methods for the preparation of N-oxides have been extensively described and reviewed in the literature, see for example: T. L. Gilchrist in *Comprehensive Organic Synthesis*, vol. 7, pp 748-750, S. V. Ley, Ed., Pergamon Press; M. Tisler and B. Stanovnik in *Comprehensive Heterocyclic Chemistry*, vol. 3, pp 18-20, A. J. Boulton and A. McKillop, Eds., Pergamon Press; M. R. Grimmett and B. R. T. Keene in *Advances in Heterocyclic Chemistry*, vol. 43, pp 149-161, A. R. Katritzky, Ed., Academic Press; M. Tisler and B. Stanovnik in *Advances in Heterocyclic Chemistry*, vol. 9, pp 285-291, A. R. Katritzky and A. J. Boulton, Eds., Academic Press; and G. W. H. Cheeseman and E. S. G. Werstiuk in *Advances in Heterocyclic Chemistry*, vol. 22, pp 390-392, A. R. Katritzky and A. J. Boulton, Eds., Academic Press.

One skilled in the art recognizes that because in the environment and under physiological conditions salts of chemical compounds are in equilibrium with their corresponding nonsalt forms, salts share the biological utility of the nonsalt forms. Thus a wide variety of salts of carboxamide arthropodicides (e.g., Formulae 1 or 2) are useful in the present compositions (i.e. are agriculturally suitable). Such salts include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic or valeric acids. Salts can also include those formed with organic bases (e.g., pyridine, triethylamine or ammonia) or inorganic bases (e.g., hydrides, hydroxides or carbonates of sodium, potassium, lithium, calcium, magnesium or barium) when the carboxamide arthropodicide contains an acidic moiety such as a carboxylic acid or phenol.

The composition of the present invention generally comprises by weight from about 0.3% to as much as 100% of a particulate component (a) comprising particles of a solid carrier infiltrated with a mixture comprising (i) one or more carboxamide arthropodicides and (ii) a surfactant constituent. Typically the present composition comprises from about 1% to about 80% and more typically from about 10% to about 60% of component (a) by weight.

As generally understood in the art of formulation, the term "surfactant" means "surface-active agent" and refers to a chemical substance or mixture of chemical substances that when added to a liquid changes the properties of that liquid at a surface. The change in properties generally comprises change, typically reduction, in surface tension.

In the present composition the surfactant constituent (ii) preferably suppresses the crystallization of the one or more carboxamides of constituent (i) to form a mixture wherein the carboxamide arthropodicide constituent (i) is at least partially amorphous. More preferably, the carboxamide arthropodicide constituent (i) is primarily (i.e. more than 50%) amorphous in the mixture of the carboxamide arthropodicide constituent (i) with the surfactant constituent (ii). Most preferably, constituent (i) is more than about 80%, 90% or even 95% amorphous in the mixture. (The aforesaid percentages are by weight; for example, if 20% by weight of constituent (i) is present in one or more crystalline phases, and thus 80% by weight is present in one or more noncrystalline (i.e. amorphous) phases, then constituent (i) is 80% amorphous.) Surfactant constituent (ii) may contain a single surfactant compound or a mixture of surfactant compounds. A variety of surfactant molecular types are useful in forming surfactant constituent (ii). However, surfactants providing best results typically have low melting points and preferably are liquids or amorphous solids at room temperature. To facilitate absorption into the solid carrier particles, surfactants of constituent (ii) are preferably soluble in solvents useful for dissolving the one or more carboxamide arthropodicides of constituent (i). Surfactants providing best results also typically are soluble in water and promote wetting. The wetting property of surfactants increases the ability of a liquid to spread and penetrate by lowering the liquid's surface tension. In the context of the present invention this wetting property can help draw water into the solid carrier particles and facilitate mobilization of the one or more carboxamide arthropodicides of constituent (i). Surfactant constituent (ii) may also have other properties known for surfactants, such as dispersant and defoaming effects.

Illustrative of the variety of surfactant molecular types that work particularly well in surfactant constituent (ii) are alkylbenzenesulfonic acids and their salts, alkylpolyglycosides, ethylene oxide-propylene oxide block copolymers, and ethoxylated sorbitan esters. The ester group in ethoxylated sorbitan ester surfactants is typically derived from a fatty acid. Examples of alkylbenzenesulfonic acids and their salts are dodecylbenzenesulfonic acid and sodium dodecylbenzenesulfonates. An example of alkylpolyglycosides is ($C_{12}$-$C_{16}$ alkyl)polyglycoside having an average degree of polymerization of 1.4 (e.g., AGNIQUE PG 264-G). An example of ethylene oxide-propylene oxide block copolymers is a block copolymer consisting of about 11 ethylene oxide-derived units, then about 16 propyleneoxide-derived units, and then about 11 ethylene oxide-derived units (e.g., PLURONIC L35). An example of ethoxylated sorbitan esters is polyoxyethylene (20) sorbitan monolaurate, i.e. sorbitan to which about 20 ethylene oxide-derived units are attached, capped with about 1 laurate ester group per molecule (e.g., TWEEN 20).

Optimal surfactants for combining with particular carboxamide arthropodicides in particulate component (a) can be identified by a simple procedure of evaporating a drop of solution containing surfactant and carboxamide arthropodicide in solvent on a microscope slide and using optical microscopy to verify lack of crystallinity indicated by birefringence and/or lack of regular shape or a shape different from that of original crystalline particles. Lack of crystallinity of the evaporated deposit can be further confirmed by such techniques as differential scanning calorimetry and x-ray diffraction.

Typically the weight ratio of constituent (ii) (i.e. the surfactant constituent) to constituent (i) (i.e. the one or more carboxamide arthropodicides) in particulate component (a) is at least about 1:2, more typically at least about 1:1. Typically the weight ratio of constituent (ii) to constituent (i) is no more than about 50:1, more typically no more than about 5:1, and most typically no more than about 2:1.

In component (a) of the present composition a mixture of constituent (i) and constituent (ii) is infiltrated (i.e. absorbed) into particles of the solid carrier. The carrier provides support for the mixture of constituents (i) and (ii) and also provides mechanical strength during further formulation processing, e.g., milling, granulation. Therefore solid carriers are formed from porous absorptive materials. The composition of the present invention is typically not used as an arthropodicidal bait, and the carrier typically does not comprise food materials attractive to arthropod pests. To absorb a desired amount of the mixture of constituent (i) and constituent (ii), typically dissolved in a solvent, the solid carrier needs to have sufficient internal surface area and intrusion volume to accommodate the mixture and also a large enough pore diameter to facilitate absorption of the mixture. Typically the intrusion volume is between 1 and 20 $cm^3/g$, more typically between 3 and 10 $cm^3/g$ and most typically between 5 and 10 $cm^3/g$. The internal surface area is typically between 20 and 400 $m^2/g$ and more typically between 100 and 200 $m^2/g$. The mean pore diameter is typically between 0.05 and 2 μm, more typically between 0.05 and 1 μm, and most typically between 0.1 and 0.5 μm. Classes of materials with such properties include precipitated, amorphous and fumed silicas, silicates of lithium, sodium, magnesium, potassium, calcium and aluminum, diatomaceous earths, and bentonite, kaolin and attapulgite clays. Examples of silicas include Degussa FK-35, SIPERNAT D-17, SIPERNAT 22 and SIPERNAT 50S (all precipitated silicas), Degussa AEROSIL 200 (a fumed silica), Davison SYLOID 244 (an amorphous silica), Johns-Manville CELITE 209 (diatomaceous earth). Examples of silicates include Johns-Manville MICROCEL E (calcium silicate), Huber HUBERSORB 600 (precipitated amorphous calcium silicate), Harbourlite Perlite 2005 (amorphous aluminum silicate) and Huber ZEOLEX 7A (sodium silicate). Examples of clays include American Colloid VOLCLAY 325 (bentonite), HUBER Barden clay (kaolin) and Englehard MICROSORB LVM (attapulgite).

Solid carriers comprising a silica compound (i.e. a silica or silicate) work particularly well in component (a) of the composition of the present invention. Therefore of note is the composition of the invention wherein the solid carrier in component (a) comprises at least one silica or silicate selected from the group consisting silicas and silicates of lithium, sodium, potassium, magnesium, calcium and aluminum (including mixtures thereof), and particularly of magnesium, calcium and aluminum (including mixtures thereof). Of particular note is calcium silicate, which is commercially available in forms (e.g., MICROCEL E) with pore size and other properties making it especially useful as a solid carrier in component (a) of the present composition.

Depending upon formulation processing, application and use of the composition, the water solubility of solid carrier in component (a) may or may not be important. If the solid carrier is readily soluble in water, dilution of the composition in water prior to spraying will typically form a dispersion of constituent (i) (i.e. the one or more carboxamide arthropodicides) instead of a dispersion of particles of the solid carrier infiltrated with a mixture comprising constituent (i) and constituent (ii) (i.e. a surfactant constituent). Although this can still provide good arthropodicidal efficacy, separation of constituent (i) from constituent (ii) can result in crystallization of constituent (i), and thus reduce efficacy. If formulation processing involves water, such as for granulating a wettable powder, the solid carrier in component (a) should be relatively water insoluble. Typically the solid carrier in component (a) of the present composition is relatively water insoluble. The expression "relatively water insoluble" in the context of the present disclosure and claims means that stirring the solid carrier in powder form in water at 20° C. for 6 h results in no more than 10 g of solid carrier dissolving in 1 L of water. Preferably under these conditions no more than about 5 g, and more preferably no more than about 2 or 1 g of solid carrier dissolves in 1 L of water. Clays, silicas and silicates of magnesium, calcium and aluminum typically have water solubility of less than, and often much less than, 2 g per L.

Pore diameter places a lower limit on particle size, as particles cannot be smaller than their pores. Therefore typically the mean particle size (i.e. volume moment mean, De Brouker mean) of the particles of the solid carrier is at least 0.1 µm and more typically at least 5 µm. The speed of absorption of the mixture of constituents (i) and (ii), typically dissolved in a solvent, may decrease with increasing particle size due to increasing distance between the particle surface and center. Furthermore, if the diluted composition is to be sprayed, the particles in the composition must be smaller than the spray head orifice. Therefore typically the mean particle size of the particles of the solid carrier is no more than 200 µm and more typically no more than 20 µm.

Typically the weight ratio of the mixture comprising one or more carboxamide arthropodicides and the surfactant constituent to the solid carrier in component (a) is at least about 1:2 and more typically at least about 2:3. As the solvent dissolving the mixture takes up volume until it is evaporated, obtaining higher weight ratios of the mixture to the solid carrier may require repeated cycles of application followed by solvent evaporation. Typically the weight ratio of the mixture to the solid carrier is no more than about 5:1, more typically no more than about 4:1 or 3:1, and most typically not more than about 2:1.

In the composition of the present invention, component (b) is a surfactant component having dispersing and wetting properties. Because constituent (ii) of component (a) itself provides surfactant properties, component (b) is optional (i.e. may be 0% of the composition). However, the one or more surfactants of constituent (ii) are generally selected primarily for their capacity to produce amorphous mixtures with the one or more carboxamide arthropodicides of constituent (i) and secondarily their wetting ability rather than ability to disperse particles on dilution with water. Furthermore surfactant constituent (ii) of component (a) may be present in only relatively small amounts, as component (a) can itself be as little as 0.3% of the composition by weight. Therefore typically the composition of the present invention comprises as component (b) up to about 50% by weight of a surfactant component having dispersing and wetting properties. The present composition more typically comprises from about 1% to about 30%, most typically from about 3% to about 15% of component (b) by weight.

In the present compositions the surfactant component (b) has both dispersing and wetting properties. Surfactant component (b) may also have other properties known for surfactants, such as defoaming effect. The dispersing property of surfactants reduces the cohesive attraction between particles of similar composition and thus the tendency of particles to stick together after dilution with water. Particles sticking together results in formation of agglomerates that do not disperse well in water. Dispersants, also called dispersing agents, can reduce attractive forces between particles in close proximity. The wetting property of surfactants increases the ability of a liquid to spread and penetrate by lowering the liquid's surface tension. Wetting as well as dispersing properties facilitate forming aqueous dispersions of particles from solid formulations. Wetting agents can also help spread spray mixtures across foliage surfaces to provide better coverage. Some surfactants have both dispersing and wetting properties. However, usually a surfactant will be most useful for either a dispersing or a wetting effect. Therefore typically the surfactant component (b) comprises a least two surfactants, at least one of which is regarded as a dispersant and at least one of which is regarded as a wetting agent.

A wide variety of dispersants and wetting agents are known in the art of formulation, including those described in *McCutcheon's Detergents and Emulsifiers Annual*, Allured Publ. Corp., Ridgewood, N.J., as well as Sisely and Wood, *Encyclopedia of Surface Active Agents*, Chemical Publ. Co., Inc., New York, 1964. Examples of dispersants include, but are not limited to, sodium, calcium and ammonium salts of lignosulfonates (optionally polyethoxylated) (e.g., MARASPERSE N22), formaldehyde condensates of naphthalene-sulfonates or alkylnaphthalenesulfonates (e.g., MORWET D425), condensed methylnaphthalenesulfonates (e.g., SUPRAGIL MNS/90), anionic condensation products of alkylphenol, formaldehyde and optionally sodium sulfite, salts of polycarboxylic acids (e.g., polyacrylic acids and copolymers) (e.g., METASPERSE 550), phosphate esters of tristyrylphenol ethoxylates (e.g., SOPROPHOR 3D33), polyethylene/polypropylene block polymers (e.g., PLURONIC F108, ATLOX 4912, ATLAS G-5000, SYNPERONIC PE series copolymers) and ethylene oxide-propylene oxide based acrylic acid graft copolymers such as methyl methacrylate graft copolymers (e.g., ATLOX 4913). Examples of wetting agents include, but are not limited to, alkyl sulfosuccinates (e.g., AEROSOL OTB), laurates, sulfate and phosphate esters of long chain alcohols, acetylenic diols, ethoxyfluorinated alcohols, ethoxylated silicones, alkyl phenol ethoxylates, benzene sulfonates, alkyl-substituted benzene sulfonates such as sodium dodecylbenzenesulfonates (e.g., RHODACAL DS10), alkyl α-olefin sulfonates, naphthalene sulfonates, alkyl-substituted naphthalene sulfonates (e.g., MORWET EFW), and alcohol ethoxylates.

Particularly useful dispersants for the compositions of the present invention include lignosulfonate salts such as MARASPERSE N22, anionic salts of acrylic acid polymers and copolymers such as METASPERSE 550 and alkyl naphthalene sulfonate formaldehyde condensates such as MORWET D425. Particularly useful wetting agents for the compositions of the present invention include anionic alkyl-substituted naphthalene sulfonates such as MORWET EFW, anionic sulfates of long chain alcohols, alkyl sulfosuccinates such as AEROSOL OTB, alkyl-substituted benzene sulfonates such as sodium dodecylbenzene sulfonate (RHODACAL DS10).

In the composition of the present invention, component (c) comprises one or more additional formulating ingredients. Although component (c) is optional (i.e. may be 0% of the present composition), typically the composition comprises at least about 1% of component (c) by weight. Although generally the composition of the present invention may comprise up to about 99.7% of component (c) by weight, typically component (c) amounts to no more than about 80%, more typically no more than about 70% of the composition by weight. The additional formulating ingredients of component (c) may be selected from the wide variety of ingredients known in the art of formulation. Many of these ingredients are described in *McCutcheon's 2001 Volume 2: Functional Materials* published by MC Publishing Company. Additional formulating ingredients include, for example, lubricants, anticaking agents, chemical stabilizers, adhesive agents, film-forming agents and solid diluents. Additional formulating ingredients particularly useful in forming the present compositions are solid diluents that are grinding aids, binders and water-soluble diluents (other than binders, film-forming agents and adhesive agents).

Grinding aids are typically brittle, non-smearing inorganic chemicals such as clays, silicas and diatomaceous earths. Grinding aids prevent build-up in mechanical impact mills. Particularly useful grinding aids in the compositions of the present invention are Barden clay, bentonite clays, attapulgite clays, and precipitated and fumed silicas. The composition of the present invention typically comprises from about 1% to about 15% of one or more grinding agents by weight of composition. Typically the one or more grinding agents in the present composition are selected from clays.

Binders increase the mechanical strength of granules by binding formulation components together. A wide variety of binders are known in the art of formulation. Particularly useful binders in the compositions of the present invention are certain saccharides and modified saccharides. These include certain sugars (e.g., sucrose), sugar derivatives (e.g., mannitol) and starches and modified starches such as dextrin. Dextrin is produced by dry roasting starch alone or in the presence of trace levels of acid catalysts (which causes hydrolysis of the starch followed by molecular rearrangement and combination of the resulting fragments). Particularly useful dextrins are yellow dextrins, which are available from many commercial sources. Yellow dextrins are typically obtained by dry roasting starch, often at temperatures above 150° C., in the presence of trace levels of acid catalysts. Yellow dextrins are yellowish powders that are substantially soluble in water near room temperature. Optimal amounts of binders can be determined by simple experimentation. When sucrose is used as the binder, it is typically included in the present composition in an amount from about 0.1% and about 5% by weight of the composition.

Film-forming agents (alternatively identified as film formers or film coating compositions) and adhesive agents (alternatively identified as adhesives or sticking agents) are used to prepare compositions for coating seeds and other propagules. These ingredients are discussed in detail below as components in coating compositions.

Water-soluble diluents rapidly dissolve in water, and thus expose the water-dispersible or soluble skeleton of the granule to water and accelerate granule break-up and dispersion. A wide range of water-soluble diluents are known in the art of formulation. These include salts or carbohydrates that dissolve rapidly in water; non-limiting examples include alkali metal phosphates, alkaline earth phosphates, sulfates of sodium, potassium, magnesium and zinc, sodium and potassium chloride, sodium benzoate, lactose and sucrose. Many of the saccharide and modified saccharide binders are water-soluble and thus promote granule break-up and dispersion on contact with water. Some water-soluble diluents have only weak binding capability and thus their principal usefulness is as water-soluble diluent. A weakly binding, water-soluble diluent particularly useful in the present composition is lactose, typically in the form of lactose monohydrate. When lactose is included, it typically is in an amount (as its monohydrate) between about 1% and about 80%, more typically between about 1% and about 35%, and most typically between about 1% and 25% of the present composition by weight.

The composition of the present invention can be formed in any of the types of solid compositions commonly used for formulating arthropodicide active ingredients. These types include dusts, powders, granules, pellets, prills, pastilles, tablets and the like. Typically the composition of the present invention is first prepared as a wettable powder. The other solid composition types can be prepared from the wettable powder using general methodologies well known in the art of formulation. For methodologies involving exposure to water, the solid carrier of component (a) should be relatively water insoluble.

A wettable powder of the composition of the present invention can be prepared by absorbing a solution of constituent (i) and constituent (ii) in a solvent onto the solid carrier, evaporating the solvent, mixing the constituent-infiltrated carrier with the other formulating ingredients, and finally milling the mixture.

Thus in the first step one or more carboxamide arthropodicides (i.e. constituent (i)) and the surfactant constituent (ii) are dissolved in a suitable solvent. Constituent (i) and constituent (ii) can be dissolved in any order. Suitable solvents are those in which constituents (i) and (ii) are soluble and stable and which are sufficiently volatile to enable solvent evaporation at temperatures not decomposing constituents (i) and (ii). Suitable solvents include pyridine and its derivatives such as 3-picoline, ethereal solvents such as tetrahydrofuran, nitrile solvents such as acetonitrile, and carboxamide solvents such as N,N-dimethylformamide (DMF), 1-methyl-2-pyrrolidinone (NMP) and 1-octyl-2-pyrrolidinone (NOP), as well as mixtures of these solvents. Hydroxylic solvents can promote hydrolysis of carboxamide arthropodicides and thus are not preferred.

The solution of constituents (i) and (ii) is then absorbed the solid carrier. Although the solid carrier can be added to the solution of constituents (i) and (ii), best results are typically achieved by slowly adding the solution to the solid carrier. On a small scale the solution can be added dropwise to the solid carrier, but on a larger scale using a spray system to apply the solution to the solid carrier may be convenient. The mixture is then typically gently stirred using, for example, a rotary mixer at low speed to thoroughly distribute the solution over the solid carrier. Because of the presence of the solvent, the infiltrated carrier powder may be sticky.

The solvent is then evaporated from the solution of constituents (i) and (ii) infiltrated into the solid carrier. To reduce the temperature needed to evaporate the solvent, the solution-infiltrated solid carrier can be subjected to vacuum (i.e. reducing the pressure below ambient). Although increasing temperature increases the rate of evaporation of the solvent, too high of temperature may promote decomposition of carboxamide arthropodicides. Preferably conditions are selected to allow evaporating the solvent at temperatures at or slightly above room temperature, for example preferably about 20-50° C. and more preferably about 20-40° C. Most preferably the solvent is evaporated at about 20-30° C. if the solvent is sufficiently volatile (i.e. has a low enough boiling point). Passing an inert gas (e.g., nitrogen) over the solution-infiltrated carrier can facilitate removal of solvent vapor. A solvent recovery system can be used to reduce cost and environmental impact.

To increase the weight ratio of the mixture of constituents (i) and (ii) to the solid carrier, the process of applying the solution of constituents (i) and (ii) to the carrier and then evaporating the solvent can be repeated one or more times.

The constituent-infiltrated carrier can be most conveniently mixed with other formulating ingredients using a blender. Premixing with a blender mixes the ingredients on a macro-scale before they are milled. Screw, paddle, cone and ribbon blenders are all suitable for premixing ingredients.

The main purpose of milling is to generate intimate contact between formulating ingredients. Many impact mills are suitable, for example, a hammer mill with a 300 US mesh screen.

In addition to wettable powders, granules are particularly useful types of solid compositions according to the present invention. Granules can be prepared starting from wettable powders using such well-known general methods as pan granulation, fluid-bed granulation and extrusion. These granulation methods typically comprise adding a granulation liquid such as water to the milled wettable powder, granulating according the particular method, and finally drying the granulated product. Pan granulation and fluid-bed granulation involve agglomeration techniques; see Browning, "Agglomeration", *Chemical Engineering*, Dec. 4, 1967, pp 147-48, *Perry's Chemical Engineer's Handbook*, 4th Ed., McGraw-Hill, New York, 1963 and U.S. Pat. No. 3,920,442. Paste extrusion involves forcing a moistened mixture, typically fed by an auger, through a die using procedures analogous to those described in PCT Patent Publication WO 2004/023876. Pellets and tablets can be prepared by dry-compressing wettable powders using a briquetting press (e.g., Model 220 Komarek Roll Briquetter, K. R. Komarek Inc., Elk Grove Village, Ill., USA), roll compactor (e.g., TF-MINI, Freund Sangyo K.K.) or tablet press using procedures analogous to those described in U.S. Pat. Nos. 4,172,714, 5,180,587, 5,208,030 and 5,232,701. For recent reviews of formulation methods, see T. S. Woods, "The Formulator's Toolbox—Product Forms for Modern Agriculture" in *Pesticide Chemistry and Bioscience, The Food—Environment Challenge*, T. Brooks and T. R. Roberts, Eds., Proceedings of the 9th International Congress on Pesticide Chemistry, The Royal Society of Chemistry, Cambridge, 1999, pp 120-133 and *Developments in Formulation Technology*, PJB Publications, Richmond, UK, 2000.

Thus as described herein, the composition of the present invention comprises as an essential element a particulate component comprising particles of a solid carrier infiltrated with a mixture comprising (i) one or more carboxamide arthropodicides and (ii) a surfactant constituent. Accordingly the mixture of one or more carboxamide arthropodicides with the surfactant constituent is absorbed into pores in the solid carrier. The pores can be in the form of channels or other cavities in the solid carrier particles, but must be open to the exterior of the particles to allow infiltration of the carboxamide arthropodicide-surfactant mixture into the particles during composition manufacture, and then later egress of the arthropodicide-surfactant mixture into a leaf cuticle, seed testa or other contacted plant part without needing to disrupt the solid carrier. The solid carrier is primarily intended to provide support, and the material of the solid carrier itself generally does not comprise either a carboxamide arthropodicide or a surfactant.

The surfactant constituent in the mixture infiltrated into the solid carrier can help draw water into the carrier particles and facilitate mobilization of the one or more carboxamide arthropodicides of constituent (i). In a preferred embodiment, the surfactant constituent suppresses the crystallinity of the one or more carboxamide arthropodicides. Maintaining a carboxamide arthropodicide in an amorphous form, particularly in mixture with a surfactant, has been discovered to facilitate absorption of the carboxamide arthropodicide into a leaf cuticle, seed testa or other plant part. The mixture comprising one or more carboxamide arthropodicides and a surfactant constituent also can comprise solvent residue left after infiltration of a solution of the arthropodicides and surfactant constituent in a solvent followed by evaporation of the solvent. The residual solvent is regarded as an impurity, not a principal component of the infiltrated mixture after evaporation. Typically the amount of residual solvent is not more than about 25%, and more typically not more than about 10% of the infiltrated mixture by weight. Typically the infiltrated mixture consists essentially of the one or more arthropodicides, the surfactant constituent and residual solvent. In the present composition the one or more carboxamide arthropodicides are typically primarily (i.e., at least about 80%, more typically at least about 90%, most typically at least about 95%) disposed within the particles of the solid carrier rather than being on the surface of the particles or between the particles.

Optionally on the surface of the particles or between the particles is a surfactant component having dispersing and wetting properties. In some embodiments one or more surfactants in this surfactant component are also present in the surfactant constituent mixed with the one or more arthropodicides, but more typically the surfactants are different. The surfactant component having dispersing and wetting properties helps disperse the infiltrated particles in an aqueous medium (e.g., in a mixture for spraying on plant foliage or propagules). As described herein, other formulating ingredients can also be present on the surface of the particles or between the particles. Water is typically present in application media (e.g., spray mixtures) and the environment. Therefore while other formulating ingredients surrounding the particles have a variety of useful functions and may have correspondingly diverse properties, they typically are selected so that the material on the surface of the particles and between the particles (all of which may be considered to be coating the particles) dissolves or disintegrates in water or at least is weakened or made porous by water, so that transfer of the carboxamide arthropodicides from the particulate component to a leaf cuticle, seed testa or other plant part is not impeded. As the mixture of the one or more carboxamide arthropodicides with the surfactant constituent in the particles can promote transfer of the carboxamide arthropodicides to plant parts, the material surrounding the particles desirably should not retard this transfer.

The composition of the present invention can be applied directly (e.g., as a dust) to the arthropod pest to be controlled (e.g., suppressed or killed) or its environment, such as plant foliage, but usually the composition is first diluted to form a dispersion in water and then sprayed on the arthropod pest or its environment. For control of phytophagous piercing-sucking arthropod pests, spraying the foliage of the plant to be protected with present composition dispersed in water facilitates absorption of the carboxamide arthropodicide active ingredient through the cuticle of the foliage. If the solid carrier is relatively water insoluble, addition of the present composition to water typically forms a suspension, i.e. a suspension of particles of the solid carrier infiltrated with a mixture comprising the one or more carboxamide arthropodicides and the surfactant constituent and also particles of other insoluble substances such clays.

The composition of the present invention can also be applied to seeds and other propagules, typically as a coating formulation also comprising a film former or adhesive agent (in component (c)). The composition of the present invention has been discovered to facilitate absorption of carboxamide arthropodicides into seeds and other propagules to protect the seeds and propagules from attack by phytophagous arthropods. Depending upon the ability of a carboxamide arthropodicide to translocate to foliage and roots developing from the propagule, these other plant parts can be protected as well. Furthermore, coating a seed or other propagule with a composition of the present invention can provide an apparent growth stimulating effect on the foliage developing from the seed or other propagule even when phytophagous arthropod pest populations in the environment appear to be insignificant.

Propagules coated with compositions of this invention include seeds. Suitable seeds include seeds of wheat, durum wheat, barley, oat, rye, maize, sorghum, rice, wild rice, cotton, flax, sunflower, soybean, garden bean, lima bean, broad bean, garden pea, peanut, alfalfa, beet, garden lettuce, rapeseed, cole crop, turnip, leaf mustard, black mustard, tomato, potato, pepper, eggplant, tobacco, cucumber, muskmelon, watermelon, squash, carrot, zinnia, cosmos, chrysanthemum, sweet scabious, snapdragon, gerbera, babysbreath, statice, blazing star, lisianthus, yarrow, marigold, pansy, impatiens, petunia, geranium and coleus. Of note are seeds of cotton, maize, soybean and rice. Propagules contacted with compositions of this invention also include rhizomes, tubers, bulbs or corms, or viable divisions thereof. Suitable rhizomes, tubers, bulbs and corms, or viable divisions thereof include those of potato, sweet potato, yam, garden onion, tulip, gladiolus, lily, narcissus, dahlia, iris, crocus, anemone, hyacinth, grape-hyacinth, freesia, ornamental onion, wood-sorrel, squill, cyclamen, glory-of-the-snow, striped squill, calla lily, gloxinia and tuberous begonia. Of note are rhizomes, tubers, bulbs and corms, or viable division thereof of potato, sweet potato, garden onion, tulip, daffodil, crocus and hyacinth. Propagules contacted with compositions of this invention also include stems and leaf cuttings.

When the present composition is applied to seeds and other propagules as a dust or powder, preferably the composition includes an adhesive agent (i.e. sticking agent) in component (c) to cause the dust or power to stick to the propagule. For coating seeds and other propagules, the present composition is preferably a film-forming formulation (i.e. composition) comprising a film former in component (c). The film coatings formed by film-forming compositions are generally more durable than coatings comprising adhesive powders.

The thickness of coatings can vary from adhering dusts to thin films to pellet layers about 0.5 to 5 mm thick. Propagule coatings according to this invention can comprise more than one adhering layers, only one of which need comprise a composition of the present invention. Generally pellets are most satisfactory for small seeds, because their ability to provide a biologically effective amount of a carboxamide arthropodicide is not limited by the surface area of the seed, and pelleting small seeds also facilitates seed transfer and planting operations. Because of their larger size and surface area, large seeds and bulbs, tubers, corms and rhizomes and their viable cuttings are generally not pelleted, but instead coated with powders or thin films.

Thus to prepare a propagule contacted with the composition of the invention and the composition is typically applied as a dust, a thin film or pellet layer. Typically the composition of this invention is applied to a propagule such that the amount of constituent (i) (i.e. one or more carboxamide arthropodicides) in the composition coating the propagule is in the range from about 0.001 to 50% of the weight of the propagule, for seeds more often in the range of about 0.01 to 50% of the seed weight, and most typically for large seeds in the range of about 0.1 to 10% of the seed weight. However, larger amount up to about 100% or more are useful, particularly for pelleting small seed for extended arthropod pest control protection. For propagules such as bulbs, tubers, corms and rhizomes and their viable cuttings, and stem and leaf cuttings, generally the composition is applied in an amount such that constituent (i) ranges from about 0.001% to 5% of the propagule weight, with higher percentages used for smaller propagules. One skilled in the art can easily determine the biologically effective amount for contacting with (i.e. applying to) the propagule necessary for the desired level of phytophagous arthropod pest control.

The film former or adhesive agent in component (c) of the present composition used to coat a propagule is preferably selected from adhesive polymers that may be natural or synthetic and are without phytotoxic effect on the propagule to be coated. The film former or sticking agent is typically selected from polyvinyl acetates, polyvinyl acetate copolymers, hydrolyzed polyvinyl acetates, polyvinylpyrrolidone-vinyl acetate copolymer, polyvinyl alcohols, polyvinyl alcohol copolymers, polyvinyl methyl ether, polyvinyl methyl ether-maleic anhydride copolymer, waxes, latex polymers, celluloses including ethylcelluloses and methylcelluloses, hydroxymethylcelluloses, hydroxypropylcellulose, hydroxymethylpropyl-celluloses, polyvinylpyrrolidones, alginates, dextrins, malto-dextrins, polysaccharides, fats, oils, proteins, karaya gum, jaguar gum, tragacanth gum, polysaccharide gums, mucilage, gum arabics, shellacs, vinylidene chloride polymers and copolymers, soybean-based protein polymers and copolymers, lignosulfonates, acrylic copolymers, starches, polyvinylacrylates, zeins, gelatin, carboxymethylcellulose, chitosan, polyethylene oxide, acrylimide polymers and copolymers, polyhydroxyethyl acrylate, methylacrylimide monomers, alginate, ethylcellulose, polychloroprene and syrups or mixtures thereof.

Methylcellulose and gum arabic are of note as adhesives (or sticking agents) in component (c) of compositions of the present invention applied to propagules as dusts or powders. Acrylic latex polymers, polyvinyl alcohol (PVA) and polyvinyl acetate (PVAc) are of particular note as film formers in component (c) of film-forming compositions of the present invention, which are applied to propagules as film coatings.

As already noted, component (c) (i.e. the one or more additional formulating ingredients) of a composition of the present invention for propagule coating typically, although not always, comprises an adhesive or film former constituent, which in the context of the present disclosure and claims denotes to a constituent consisting of one or more adhesive agents and/or film formers. Typically the adhesive or film former constituent is in an amount of between about 1% and about 90% of the composition by weight. More typically the adhesive or film former constituent is in amount between about 3% and about 75%, and most typically between about 9% and 50% of the composition by weight. The amount of the adhesive or film former constituent in the composition applied to the propagule is generally in the range of about 0.001 to 100% of the weight of the propagule. For large seeds the amount of adhesive or film former constituent is typically in the range of about 0.05 to 5% of the seed weight; for small seeds the amount is typically in the range of about 1 to 100%, but can be greater than 100% of seed weight in pelleting. For other propagules the amount of the adhesive or film former constituent is typically in the range of 0.001 to 2% of the propagule weight. In a composition of the present invention used as a film-forming formulation (i.e. propagule film coating), typically the weight ratio of component (a) to the film former in component (c) is in a range from about 100:1 to about 1:10, more typically in a range from about 30:1 to about 1:3, and most typically in a range from about 10:1 to about 1:1.

In addition to one or more film formers or sticking agents, component (c) of the present composition used as propagule coating can also comprise other formulating ingredients. Solid carriers (e.g., wood flours, clays, activated carbon, diatomaceous earth, fine-grain inorganic solids, calcium carbonate) are particularly useful in compositions used for pelleting (i.e. forming a thick layer around a propagule, typically a seed). Clays and inorganic solids which can be used include, for example, calcium bentonite, kaolin, china clay, talc, perlite, mica, vermiculite, silicas, quartz powder, montmorillonite and mixtures thereof. A composition of the present invention particularly useful as a film-forming formulation typically contains little or no solid carrier in component (c); however, component (a) itself comprises a particulate component comprising particles of a solid carrier. Component (c) of a composition of the present invention for propagule coating typically comprises at least one dye (e.g., Acid Blue 1, Pro-lzed® Colorant Red) to visually indicate that the propagule has been treated with a plant protection agent.

A composition of the present invention for coating a propagule can include component (b) (i.e. a surfactant component having dispersing and wetting properties). Component (b) can facilitate dispersion of the particles of component (a) and wetting of the propagule during the coating process.

Conventional means of applying seed coatings can be used to carry out coating with a composition of the present invention. Dusts or powders can be applied by tumbling the propagule with a composition of the present invention comprising a sticking agent in component (c) to cause the dust or powder to adhere to the propagule and not fall off during packaging or transportation. Dusts or powders can also be applied by adding a dust or powder comprising component (a) directly to the tumbling bed of propagules, followed by spraying a carrier liquid, e.g., an aqueous mixture comprising component (c) and optionally component (b), onto the seed and drying. Dusts and powders can also be applied by treating (e.g., dipping) a least a portion of the propagule with a solvent such as water, optionally comprising a sticking agent as component (c), and dipping the treated portion into a supply of the dry dust or powder comprising component (a). This method can be particularly useful for coating stem cuttings.

In an embodiment of particular note, propagules are coated with a composition in the present invention in the form of a film, i.e. film coating. As already discussed, a composition of the present invention suitable for use as a film-forming formulation generally comprises a film former in component (c). Typically component (a) is first prepared in the form of a wettable powder by absorbing a solution of constituent (i) and constituent (ii) in a solvent onto the solid carrier and then evaporating the solvent, as already described. Also an aqueous mixture is prepared comprising component (c) containing at least one film former and also typically at least one dye, and optionally component (b) (i.e. a surfactant component having dispersing and wetting properties). The wettable powder is then mixed into the aqueous mixture to form an aqueous suspension concentrate (i.e. an aqueous suspension). The aqueous suspension concentrate can also be formed using different orders of addition of component (a), component (c), water and optionally component (b). The aqueous suspension concentrate is then applied to the propagules (e.g., seeds), and the water evaporated to leave the composition of the present invention as a film on the surface of the propagule. Drying should be conducted in a way not to injure the propagule or induce premature germination or sprouting.

This process is particularly useful for applying film coatings to seeds. For coating seed, the seed and coating material are mixed in any of a variety of conventional seed coating apparatus. Various coating machines and processes are available to one skilled in the art. Suitable processes include those listed in P. Kosters et al., *Seed Treatment: Progress and Prospects,* 1994 BCPC Monograph No. 57 and the references listed therein. Three well-known techniques include the use of drum coaters, fluidized bed techniques and spouted beds. Propagules such as seeds may be pre-sized prior to coating. After coating the propagules are dried and then optionally sized by transfer to a sizing machine. These machines are known in the art for example, a typical machine used when sizing corn (maize) seed in the industry.

Using conventional seed coating apparatus, the aqueous suspension concentrate is typically sprayed onto the seeds. A two-fluid nozzle (i.e. having a gas inlet and a liquid inlet) works well for spraying aqueous suspension concentrates. Common seed coating apparatus designs present the seeds to the nozzle by tumbling them in a rotating pan or fluidizing them in a fluid bed coater. For large oblong seeds such as that of cotton, a satisfactory seed coating apparatus comprises a rotating type pan with lifting vanes turned at sufficient speed to maintain a rolling action of the seed, facilitating uniform coverage. The rate of rolling and application of coating depends upon the seed. For seed coating formulations applied as liquids (e.g., aqueous suspension concentrates), the seed coating should be applied over sufficient time to allow drying to minimize clumping of the seed. Using forced air or heated forced air can allow increasing the rate of application. One skilled in the art will also recognize that this process may be a batch or continuous process. As the name implies, a continuous process allows the seeds to flow continuously throughout the product run. New seeds enter the pan in a steady stream to replace coated seeds exiting the pan.

The composition of the present invention is not limited to thin film coating and may also be used for seed pelleting. The pelleting process typically increases the seed weight from 2 to 100 times and can be used to also improve the shape of the seed for use in mechanical seeders. A composition of the present composition for pelleting generally comprises in component (c), a solid diluent, which is typically an insoluble particulate material, such as clay, ground limestone, powdered silica, etc. to provide bulk in addition to a binder such as an artificial polymer (e.g., polyvinyl alcohol, hydrolyzed polyvinyl acetates, polyvinyl methyl ether, polyvinyl methyl ether-maleic anhydride copolymer, and polyvinyl-pyrrolidinone) or natural polymer (e.g., alginates, karaya gum, jaguar gum, tragacanth gum, polysaccharide gum, mucilage). After sufficient layers have been built up, the coat is dried and the pellets graded. A method for producing pellets is described in Agrow, *The Seed Treatment Market,* Chapter 3, PJB Publications Ltd., 1994.

Without further elaboration, it is believed that one skilled in the art using the preceding description can utilize the present invention to its fullest extent. The following Examples are, therefore, to be construed as merely illustrative, and not limiting of the disclosure in any way.

FORMULATION EXAMPLES

Examples 1-10 describe preparation of compositions of the present invention. Comparative Examples 1-2 describe preparation of compositions made for comparative purposes.

The identities of proprietary ingredients used in these compositions are described in Table 1. The IKA M20 mill referred to in the preparation descriptions was a Model M20 S3 Universal Mill (Universalmuehle) manufactured by IKA Labortechnik, Stauffen, Germany. This mill comprises a rapidly revolving blade cutter in a grinding chamber.

TABLE 1

Identity of Ingredients used in Examples

| Name | Identity |
| --- | --- |
| Compound 1 | 3-Bromo-1-(3-chloro-2-pyridinyl)-N-[4-cyano-2-methyl-6-[(methylamino)carbonyl]phenyl]-1H-pyrazole-5-carboxamide |
| Compound 2 | 3-bromo-N-[4-chloro-2-methyl-6-[(methylamino)carbonyl]phenyl]-1-(3-chloro-2-pyridinyl)-1H-pyrazole-5-carboxamide |
| MICROCEL E (Johns-Manville) | Porous calcium silicate powder |
| AGNIQUE PG 264-G (Cognis) | ($C_{12}$-$C_{16}$ alkyl)polyglycoside, average degree of polymerization of 1.4, contains about 48% water |
| PLURONIC L35 (BASF Wyandotte) | Block copolymer of ethylene oxide and propylene oxide (EO11-PO16-EO11) |
| DISCO L244 (Incotec) | Proprietary film coating composition |
| TERSPERSE 2500 (Huntsman Performance Products) | Acrylic graft co-polymer |
| TWEEN 20 (Uniqema) | Polyoxyethylene (20) sorbitan monolaurate |
| MARASPERSE N22 (Uniqema) | Calcium lignosulfonate |
| MORWET D425 (Witco) | Sulfonate of naphthalene formaldehyde condensate, sodium salt |
| Barden Clay | Kaolin clay |
| MORWET EFW (Witco) | Sodium alkylnaphthalenesulfonate |
| RHODACAL BX78 (Rhodia) | Sodium dibutylnaphthalenesulfonate |
| REAX 88B (MeadWestvaco) | Sodium lignosulfonate (highly sulfonated kraft lignan polymer) |
| CAB-O-SIL M5 (Cabot Corp.) | Fumed silica |

The sample of Compound 1 used in the present Examples and Comparative Examples was prepared as described in Reference Example 1. Amounts listed for Compound 1 refer the amount of technical grade ("tech. grade") material. The assay of Compound 1 in the technical material varied slightly due to the ability of the material to adsorb varying amounts of water. HPLC analysis of the particular sample used to prepare Comparative Examples 1 and 2 indicated the technical grade material contained 93.4% Compound 1 by weight. The sample of Compound 2 used in the present Examples was prepared by one or more of the methods described in PCT Publications WO 03/015519 A1 and WO 2006/062978, and melted in the range between 232 and 235° C.

Reference Example 1

Preparation of 3-bromo-1-(3-chloro-2-pyridinyl)-N-[4-cyano-2-methyl-6-[(methylamino)-carbonyl]phenyl]-1H-pyrazole-5-carboxamide (Compound 1)

To a mixture of 3-bromo-1-(3-chloro-2-pyridinyl)-1H-pyrazole-5-carboxylic acid (20.6 kg) and 2-amino-5-cyano-N,3-dimethylbenzamide (14.1 kg) in acetonitrile (114 kg) was added 3-picoline (22.2 kg). The mixture was cooled to −10 to −14° C., and then methanesulfonyl chloride (10.6 kg) was slowly added so that the temperature did not exceed 5° C. After reaction completion as ascertained by HPLC and NMR analyses, the mixture was worked up by successively adding water (72.6 kg) and concentrated hydrochloric acid (7.94 kg) at such a rate that the temperature did not exceed 5° C. After being maintained at a temperature not exceeding 5° C. for about 30 minutes, the reaction mixture was filtered to collect the solid product, which was successively washed with acetonitrile-water (2:1, 2×12.3 kg) and acetonitrile (2×10.4 kg). The solid was then dried at about 50° C. under reduced pressure and a flow of nitrogen gas to give the title product as a white crystalline solid, which was directly used in the present formulation Examples and Comparative Examples. With a moderate rate of heating (heating to about 150° C. over 5 minutes and then decreasing rate of heating from about 4-5° C./minute to about 3° C./minute to reach 210° C. over about 15 minutes more) to facilitate volatilization of loosely entrained solvents from the solid product, melting occurred in the range between 204 and 210° C.

Examples 1-5

Wettable Powder Formulations

Table 2 lists weight percentage amounts of ingredients used to prepare compositions according to the present invention. The compositions of Examples 1-5 were prepared on a 10 g scale, and therefore the amounts of ingredients used were 10 g multiplied by the listed percentages. In Examples 1-5 surfactants were selected from AGNIQUE PG 264-G, dodecylbenzenesulfonic acid, PLURONIC L35, sodium dodecylbenzenesulfonate and TWEEN 20 as the surfactant constituent (ii) of the present compositions. According to the general procedure followed, 0.15 g of the selected surfactant was added to between 2.3 and 3 g of 3-picoline solution containing 5% technical grade Compound 1 in a 10-mL glass vial. The suspension was mixed to dissolve the surfactant. The resulting solution was added dropwise to 2-3 g of MICROCEL E in a 10-mL glass vial while gently stirring the mixture by hand with a spatula until the mixture became sticky and no longer free flowing. The mixture was then placed in a vacuum oven (at room temperature and under vacuum at 2.7-3.1 kPa pressure) which was purged with nitrogen gas to remove the 3-picoline solvent. The resulting material was then sieved through a 16-mesh (US) stainless steel screen to reduce particle size and make the material more homogeneous prior to further formulation. The sieved powder was transferred into a plastic bag, and the appropriate amounts of MORWET EFW, MARASPERSE N22, MORWET D425, Barden clay, sucrose and lactose monohydrate were added. The bag was closed and then inverted several times to blend the ingredients. The mixture was milled for 15 seconds in the IKA M20 mill, and then the finished product was collected.

Table 2 also lists the concentration of Compound 1 in each finished product. To determine the concentration, an approximately 1.2-g sample of finished product was added to 80 mL of an 80:20 (volume) mixture of acetonitrile and tetrahydrofuran. The mixture was then sonicated for about 10 minutes in an ultrasonic bath and allowed to come to room temperature. The mixture was then diluted to 100 mL by adding 80:20 acetonitrile-tetrahydrofuran and filtered through an ACRODISC 0.2 μm pore size polytetrafluoroethylene (PTFE) membrane (Pall Corp., East Hills, N.Y., USA). The filtrate was then promptly analyzed using reversed-phase liquid chromatography with a 15-cm ZORBAX SB-Phenyl (3.5 μm particles) column (Agilent Technologies, Santa Clara, Calif., USA), elution with mixtures of acetonitrile and water adjusted to pH 2.5 using phosphoric acid, and UV detection at 260 nm. The weight percent of Compound 1 in each sample was determined based on a peak area-concentration curve created by analysis of solutions of Compound 1 of known concentrations.

TABLE 2

Percentage Amounts of Ingredients Used to Prepare the Compositions of Examples 1-5, and Assay of Compound 1 in Prepared Compositions

| | Example | | | | |
|---|---|---|---|---|---|
| Surfactant Constituent (ii) | 1 AGNIQUE PG 264-G | 2 Dodecylbenzene-sulfonic acid | 3 PLURONIC L35 | 4 Sodium dodecyl-benzenesulfonate | 5 TWEEN 20 |
| Amount | 1.16 | 1.29 | 1.49 | 1.41 | 1.24 |
| Compound 1, tech. grade | 1.16 | 1.29 | 1.49 | 1.41 | 1.24 |
| MICROCEL E | 18.18 | 17.92 | 17.52 | 17.68 | 18.02 |
| MORWET EFW | 0.50 | 0.50 | 0.50 | 0.50 | 0.50 |
| MARASPERSE N22 | 3.00 | 3.00 | 3.00 | 3.00 | 3.00 |
| MORWET D425 | 7.00 | 7.00 | 7.00 | 7.00 | 7.00 |
| Barden Clay | 7.00 | 7.00 | 7.00 | 7.00 | 7.00 |
| Sucrose | 1.00 | 1.00 | 1.00 | 1.00 | 1.00 |
| Lactose monohydrate | 61.50 | 61.50 | 61.50 | 61.50 | 61.50 |
| Compound 1 Assay | 1.051 | 0.918 | 1.273 | 1.140 | 1.044 |

Comparative Examples 1-2

For comparison, two wettable granule formulations not comprising particles of a solid carrier infiltrated with one or more carboxamide arthropodicides and a surfactant constituent were prepared. The ingredients were weighed into a plastic bag according to the proportions specified in Table 3 to prepare 700 g of premix. The ingredients were manually blended by inverting the closed bag several times. Then the entire contents of the bag was milled using a hammer mill with 60 mesh screen. The milled premix was transferred to a paddle kneader, and sufficient water was added to bring the moisture content to 12%. The moistened premix was kneaded in the paddle kneader for 4 minutes and then was transferred to a volumetric screw feeder. The screw feeder moved the premix at a rate of about 450 g/min to a dome extruder. Extruded granules were collected and dried using a fluid bed dryer. Granules obtained by this procedure with the ingredients listed in Table 3 extruded easily and dispersed rapidly in water.

TABLE 3

Percentage Amounts of Ingredients Used to Prepare the Compositions of Comparative Examples 1-2

| | Comparative Example | |
|---|---|---|
| | 1 % | 2 % |
| Compound 1, tech. grade | 37.0 | 53.8 |
| RHODACAL BX78 | 0.5 | 0.5 |
| MARASPERSE N22 | 3.0 | 3.0 |
| REAX 88B | 6.0 | 6.0 |
| CAB-O-SIL M5 | 0.5 | 0.5 |
| Barden Clay | 2.0 | 2.0 |
| Sucrose | 1.0 | 1.0 |
| Lactose monohydrate | 50.0 | 33.2 |

Examples 6-10

Coating Maize Seeds

In these Examples, the wettable powder component of each seed coating composition was prepared from the relative amounts of Compound 2, MICROCEL E and TERSPERSE 2500 surfactant listed in Table 4 below.

TABLE 4

Percentage Amounts of Nonvolatile Ingredients Used to Prepare the Wettable Powder Components for Coated Seeds of Examples 6-10

| Example | 6 | 7 | 8 | 9 | 10 |
|---|---|---|---|---|---|
| Compound 2, tech. grade | 20 | 10 | 14 | 14 | 10 |
| MICROCEL E | 60 | 50 | 72 | 72 | 50 |
| TERSPERSE 2500 | 20 | 40 | 14 | 14 | 40 |

A solution of Compound 2 (technical grade) and TERSPERSE 2500 surfactant in N,N-dimethylformamide (DMF, 2 g per g of MICROCEL E) was added dropwise to MICROCEL E in a 10-mL glass vial while gently stirring the mixture by hand with a spatula. Then the solvent was evaporated by using a vacuum oven (at 40° C. and under vacuum at 2.7-3.1 kPa pressure) and purging the DMF with a flow of nitrogen gas. The resulting material was then sieved through a 16-mesh (US) stainless steel screen to reduce particle size and make the material more homogeneous prior to formulating.

The resulting wettable powder (0.206 g for Examples 6, 7, 9 and 10, and 0.412 g for Example 8) for each seed coating composition was incorporated into a mixture of water (5.0 g) and DISCO L244 film coating composition (0.087 g) to form an aqueous suspension concentrate, which was mixed using a rotor-stator mixer for 30 s at 14,000 rpm. The aqueous suspension concentrate was sprayed at a rate of 1 mL/minute onto 100 corn (maize) seeds tumbling in a pan oriented at a 45-degree angle and rotating at 20 revolutions per minute (rpm). Hot air was blown over the seeds to remove water and keep the seeds from sticking together.

The average amount of active ingredient applied per seed was analytically measured by ultrasonically extracting with tetrahydrofuran a sample of 4 treated seeds. The amount of Compound 2 in the extract was determined by reversed-phase liquid chromatography using a 4.6 mm×15 cm ACE 3 C18 Ultra Inert Base Deactivated Analytical HPLC Column having 3-μm particle size (Catalog No. ACE-111-1546, MacMod Analytical Inc., Chadds Ford, Pa., USA), mixtures of pH 3-buffered water and acetonitrile as eluant, UV detection at 275 nm, phenyl sulfone as internal standard, and calibration curves (peak area ratio vs. amount ratio) prepared from analysis of standard solutions. Dividing the amount of extracted Compound 2 by the number of seeds determined the average amount of active ingredient per seed, which is listed in Table 5.

TABLE 5

Average Amounts of Compound 2 in Coated Seeds of Examples 6-10

| Example | 6 | 7 | 8 | 9 | 10 |
|---|---|---|---|---|---|
| Compound 2 (mg a.i.) | 0.09 | 0.09 | 0.12 | 0.09 | 0.10 |

Biological Examples of the Invention

Test A

Cotton plants grown in Redi-earth media (one plant per pot) were used for testing. Test plants with two true leaves were introduced into cages where adults of silverleaf whitefly (*Bemisia argentifolii*) were allowed to lay eggs for approximately 24 h. Only plants showing egg lay were used for testing of formulated compositions. Prior to application of the compositions, plants were checked again for egg hatch and crawler (newly hatched whitefly immature) settlement. One leaf per plant was considered as one replication; four replications were used per treatment.

All formulated compositions were mixed in water using four different concentrations of each composition. Plants were sprayed using a TeeJet flat fan spray nozzle positioned 19 cm above the tallest plant. Spray flow provided an application rate equivalent to 468 L/ha. After spraying, plants were allowed to dry in a ventilated enclosure and then moved to a growth chamber operated with 16/8 h daytime/night photoperiod and 28/24° C. daytime/night temperatures and 50% relative humidity.

Evaluations were made 6 days after plants were sprayed. All leaves were removed from each test plant, and the dead and live nymphs present on the underside of each leaf were counted. The data was analyzed by Logit/Probit dose response/mortality regression, and lethal concentrations $LC_{50}$ and $LC_{90}$ were calculated in units of g a.i./ha based on the assay of Compound 1 in the completed formulated compositions. Each Table (Tables A1, A2) corresponds to a set of one or more concurrent tests. $LC_{50}$ and $LC_{90}$ values are presented rounded to two significant figures, but the compositions of Comparative Examples 1 and 2 exhibited so little activity that only lower bounds for $LC_{50}$ and $LC_{90}$ could be meaningfully determined.

TABLE A1

Lethal concentrations of Compound 1 formulated in Comparative Examples in controlling silverleaf whitefly on cotton (*)

| Composition | $LC_{50}$ | $LC_{90}$ |
|---|---|---|
| Comparative Example 1 | >6000 | >190000 |
| Comparative Example 2 | >9000 | >220000 |

(*) LC values are in g a.i./ha. Only lower bounds could be determined, as the comparative formulations showed little activity in this test.

TABLE A2

Lethal concentration of Compound 1 formulated in Examples 1-5 in controlling silverleaf whitefly on cotton (*)

| Composition | $LC_{50}$ | $LC_{90}$ |
|---|---|---|
| Example 1 | 110 | 270 |
| Example 2 | 94 | 230 |
| Example 3 | 210 | 820 |
| Example 4 | 110 | 250 |
| Example 5 | 220 | 1400 |

(*) LC values are in g a.i./ha.

As can be seen from the results of Table A1, the compositions of Comparative Examples 1 and 2 exhibited little activity controlling silverleaf whitefly in this test. In contrast, all of the compositions of the present invention showed significant activity. Table A2 shows that even the compositions of Examples 3 and 5, which exhibited the least activity of the present compositions tested, provided 90% kill of whitefly at application rates of less than 2 kg a.i./ha. Furthermore, the compositions of Examples 1, 2 and 4 provided 90% kill of whitefly at application rates of less than 300 g a.i./ha.

Test B

Corn (maize) seeds coated with compositions of the present invention according to Examples 6 through 10 as well as untreated seeds as controls were planted in an outside field. Each treatment and the control involved 16 corn plants. When the plants had produced six leaves the third and fifth leaves were excised for testing against *Spodoptera frugiperda*. The leaves were cut and placed into wells (one piece per well) of a 16-well translucent plastic tray. One third-instar *S. frugiperda* larva was also placed in each well. The trays were held in a growth chamber (16 h/8 h light/dark cycle, 25° C., 50% RH). Insect mortality and leaf feeding damage were determined 96 h after the infestation. In Table B1 insect mortality is reported on a 0 to 100 percent scale in which 0 means no effect and 100 means 100% mortality. In Table B1 larval leaf feeding is reported on a 0 to 100 percent scale in which 0 means no larval consumption of the leaf and 100 means complete consumption of the leaf.

The corn plants were further grown in the field until they produced their ninth leaf Phytophagous arthropod pest populations appeared to be low, and even the foliage of the untreated control plants did not obviously exhibit substantial arthropod damage. The corn stalks were cut at ground level and weighed. Average fresh stalk weight for each treatment and the control are reported in Table B2.

TABLE B1

Effect of Seed Coating Compositions on Mortality and Leaf Feeding of S. frugiperda larvae

| Seed Coating Composition | Average amount of active ingredient (mg ai/seed) | Percent Larval Mortality | Percent Larval Leaf Feeding |
|---|---|---|---|
| Example 6 | 0.09 | 63 | 10 |
| Example 7 | 0.09 | 41 | 19 |
| Example 8 | 0.12 | 59 | 12 |
| Example 9 | 0.09 | 63 | 10 |
| Example 10 | 0.10 | 42 | 16 |
| No seed coating | 0.00 | 0 | 100 |

Table B1 shows seed treatments with a composition of the present invention providing sufficient concentrations of Compound 2 in the developing foliage to kill substantial numbers of S. frugiperda larvae and greatly reduce leaf feeding.

TABLE B2

Effect of Seed Coating Compositions on Corn Growth

| Seed Coating Composition | Average amount of active ingredient (mg ai/seed) | Average Plant Fresh Weight (g) |
|---|---|---|
| Example 6 | 0.09 | 27.2 |
| Example 7 | 0.09 | 26.3 |
| Example 8 | 0.12 | 25.3 |
| Example 9 | 0.09 | 20.3 |
| Example 10 | 0.10 | 19.6 |
| No seed coating | 0.00 | 17.0 |

Table B2 shows that under field conditions, corn seeds treated with a composition of the present invention produced corn plants having substantially greater plant weights even though the foliage of the untreated corn plants did not appear to exhibit substantial arthropod damage.

What is claimed is:

1. A solid arthropodicide composition comprising by weight
   (a) from 0.3 to 100% of a particulate component comprising porous particles of a solid carrier selected from the group consisting of silicas and silicates of magnesium, calcium, aluminum and mixtures thereof infiltrated with a mixture comprising (i) an anthranilamide of Formula 1, wherein
   X is N;
   $R^1$ is $CH_3$;
   $R^2$ is Cl or —CN;
   $R^3$ is Br;
   $R^{4a}$ is $CH_3$ or 1-cyclopropylethyl;
   $R^{4b}$ is H;
   $R^5$ is Cl; and
   $R^6$ is H;
   and (ii) a surfactant constituent selected from the group consisting of; dodecylbenzenesulfonic acid, sodium dodecylbenzenesulfonate; a ($C_{12}$-$C_{16}$ alkyl)polyglycoside; an ethylene oxide-propylene oxide block copolymer consisting of 11 ethylene oxide-derived units, then 16 propylene oxide block copolymers and then 11 ethylene oxide-derived units; and polyoxyethylene (20) sorbitan monolaurate, wherein the weight ratio of the surfactant constituent (ii) to the anthranilamide of Formula 1 (i) ranges from 1:2 to 2:1.

2. The composition of claim 1 wherein the (i) anthranilamide of Formula 1 is 3-bromo-1-(3-chloro-2-pyridinyl)-N-[4-cyano-2-methyl-6-[(methylamino)carbonyl]phenyl]-1H-pyrazole-5-carboxamide or 3-bromo-N-[4-chloro-2-methyl-6-[(methylamino)carbonyl]phenyl]-1-(3-chloro-2-pyridinyl)-1H-pyrazole-5-carboxamide.

3. The composition of claim 1 wherein (i) the anthranilamide of Formula 1 is 3-bromo-1-(3-chloro-2-pyridinyl)-N-[4-cyano-2-methyl-6-[(methylamino)carbonyl]phenyl]-1H-pyrazole-5-carboxamide.

4. The composition of claim 1 wherein the solid carrier is calcium silicate.

5. The composition of claim 1 further comprising from 1 to 99.7% of one or more additional formulating ingredients.

6. The composition of claim 5 wherein the one or more additional formulating ingredients comprise one or more clays in an amount ranging from 1 to 15% of the composition by weight.

7. The composition of claim 5 wherein the one or more additional formulating ingredients comprise one or more saccharides in an amount ranging from 1 to 85% of the composition by weight.

8. The composition of claim 5 wherein the one or more additional formulating ingredients comprise an adhesive or film former constituent in an amount ranging from 1 to 90% of the composition by weight.

9. The composition of claim 1 wherein the weight ratio of the surfactant constituent (ii) to the one or more carboxamide arthropodicides (i) is 1:1.

10. The composition of claim 1 further comprising 1 to 50% of a surfactant component (b) selected from the group consisting of sodium alkylnaphthalenesulfonate, sodium salt of naphthalene formaldehyde sulfonate and calcium lignosulfonate present on the surface of the particles or between the particles of the solid carrier, said surfactant component having dispersing and wetting properties.

11. A plant propagule contacted with a biologically effective amount of the composition of claim 1.

12. The propagule according to claim 11 which is a seed.

13. The propagule of claim 12 which is a seed of cotton, maize, soybean or rice.

* * * * *